United States Patent [19]

Schumacher et al.

[11] Patent Number: 5,539,088
[45] Date of Patent: Jul. 23, 1996

[54] WATER-SOLUBLE AZO COMPOUNDS, CONTAINING A DIAZO COMPONENT WITH A HETEROCYCLIC MOIETY, AND A COUPLING COMPONENT WITH A FIBRE-REACTIVE GROUP, SUITABLE AS DYESTUFFS

[75] Inventors: Christian Schumacher, Frankfurt; Werner H. Russ, Flörsheim, both of Germany

[73] Assignee: Hoechst Aktiengesellschaft, Frankfurt, Germany

[21] Appl. No.: 382,645

[22] Filed: Feb. 2, 1995

[30] Foreign Application Priority Data

Feb. 4, 1994 [DE] Germany .......................... 44 03 395.8
Dec. 2, 1994 [DE] Germany .......................... 44 42 947.9

[51] Int. Cl.⁶ .......................... C09B 62/006; C09B 62/08; C09B 62/507; D06P 1/38
[52] U.S. Cl. .......................... 534/633; 534/635; 534/642; 8/543; 8/549
[58] Field of Search .......................... 534/635, 642, 534/779, 789; 8/543, 549

[56] References Cited

U.S. PATENT DOCUMENTS 4,377,518   3/1983   Vor der Bruck et al. .......... 534/617 X
5,200,512   4/1993   Reiher ...................... 534/635

FOREIGN PATENT DOCUMENTS 54-61230   5/1979   Japan ...................... 534/635

OTHER PUBLICATIONS

Naik et al., *Chemical Abstracts*, 112:8700e (1990).

*Primary Examiner*—Fiona T. Powers
*Attorney, Agent, or Firm*—Connolly and Hutz

[57] ABSTRACT

Water-soluble azo compounds are described which possess fiber-reactive properties and which are suitable as dyes for the dyeing of material, in particular fiber material, which contains hydroxy and/or carboxamido groups, examples being cellulosic fiber materials such as cotton, wool and nylon, and which compounds possess, as the radical of a diazo component, a radical of the formula

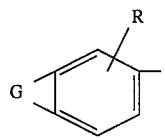

in which R is hydrogen, alkyl of 1 to 4 carbon atoms, alkoxy of 1 to 4 carbon atoms, halogen or sulfo and G forms to the benzene ring the radical of a heterocycle which is free from olefinic double bonds and which contains at least one carboxamide group of the formula $-CO-N(R^{10})-$ in which $R^{10}$ is hydrogen, alkyl of 1 to 4 carbon atoms or aryl of 6 to 10 carbon atoms which maybe substituted by from 1 to 3 substituents from the group consisting of sulfo, carboxy, alkoxy of 1 to 4 carbon atoms, alkyl of 1 to 4 carbon atoms, halogen, cyano, nitro and amino, and which if desired possesses 1 or 2 further hetero-groups from the series consisting of $-O-$, $-S-$ and $-N(R^{10})-$ where $R^{10}$ is as defined, and which compounds contain a fiber-reactive radical which is attached to the coupling component by an amino group.

19 Claims, No Drawings

WATER-SOLUBLE AZO COMPOUNDS, CONTAINING A DIAZO COMPONENT WITH A HETEROCYCLIC MOIETY, AND A COUPLING COMPONENT WITH A FIBRE-REACTIVE GROUP, SUITABLE AS DYESTUFFS

The invention is in the technical field of fiber reactive dyes.

The object of the present invention was to find new fiber-reactive dyes which satisfy the heightened quality requirements of the industry and which provide dyeings in brilliant shades and with very good use fastness properties with a high degree of fixation.

The present invention provides new azo compounds having such good fiber-reactive dye properties. The new azo compounds are of the formula (1)

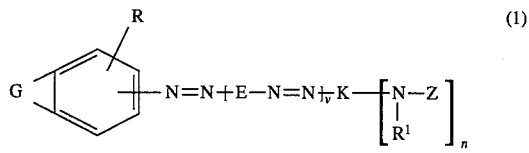

in which:

G forms to the benzene ring the radical of a heterocycle which is free from olefinic double bonds and which contains at least one carboxamide group of the formula —CO—N($R^{10}$)— in which $R^{10}$ is hydrogen, alkyl of 1 to 4 carbon atoms such as methyl and ethyl, or aryl of 6 to 10 carbon atoms, such as phenyl or naphthyl, optionally substituted by from 1 to 3 substituents from the group consisting of sulfo, carboxyl, alkoxy of 1 to 4 carbon atoms such as methoxy, alkyl of 1 to 4 carbon atoms such as methyl, halogen such as chlorine, cyano, nitro and amino, and which may possess 1 or 2 further hetero-groups from the series consisting of —O—, —S— and —N($R^{10}$)— where $R^{10}$ is as defined above, and is preferably a group of the formula (2a), (2b), (2c), (2d), (2e), (2f), (2g) or (2h)

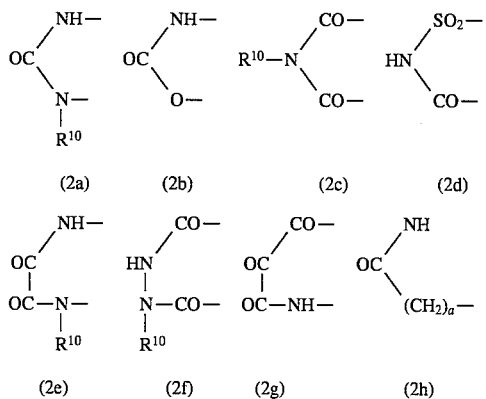

in which $R^{10}$ is as defined above and in formula (2h) the index a is the number 1 or 2;

R is hydrogen, alkyl of 1 to 4 carbon atoms such as ethyl and, in particular, methyl, alkoxy of 1 to 4 carbon atoms such as ethoxy and, in particular, methoxy, halogen such as chlorine or bromine, or sulfo, preferably hydrogen;

$R^1$ is hydrogen, alkyl of 1 to 4 carbon atoms such as ethyl and, in particular, methyl, or alkyl of 1 to 4 carbon atoms such as, in particular, ethyl which is substituted by hydroxy, cyano, alkoxy of 1 to 4 carbon atoms such as ethoxy and methoxy, carboxy, sulfo, sulfato or phosphato, or is phenyl or naphthyl, each of which may be substituted by 1, 2 or 3 substituents from the group consisting of halogen such as chlorine and bromine, hydroxy, cyano, alkoxy of 1 to 4 carbon atoms such as ethoxy and, in particular, methoxy, alkyl of 1 to 4 carbon atoms such as ethyl and, in particular, methyl, alkoxycarbonyl of 2 to 5 carbon atoms such as ethoxycarbonyl and methoxycarbonyl, carboxy, sulfamoyl, sulfo and alkylsulfonyl having an alkyl radical of 1 to 4 carbon atoms such as methyl sulfonyl and ethyl sulfonyl, and among these preferably alkoxy of 1 to 4 carbon atoms, alkyl of 1 to 4 carbon atoms, carboxy and sulfo;

E is the bivalent radical, free from the amino group, of a compound from the aniline or naphthylamine series which is capable of coupling and can be diazotized;

v is the number zero, 1 or 2, preferably zero or 1 and, with particular preference, zero;

K is the bivalent radical, free from the amino group, of a coupling component from the aniline or naphthylamine series or the bivalent radical of a coupling component from the heterocyclic series;

n is the number 1, 2, 3 or 4, preferably 1 or 2 and, with particular preference, 1;

Z is the fiber-reactive radical of a fiber-reactive group —N($R^1$)-Z, in which case, if n is greater than 1, it is possible for the radicals —N($R^1$)-Z to have definitions which are different from one another;

the compounds of the formula (1) possess at least one and preferably a plurality of, such as two, three, four or five, sulfo groups.

The radical $R^{10}$ is preferably methyl, ethyl, phenyl, monosulfophenyl, disulfophenyl, trisulfophenyl, naphthyl, monosulfonaphthyl, disulfonaphthyl or trisulfonaphthyl and, with particular preference, hydrogen.

Of the abovementioned radicals of the formulae (2a) to (2h), those of the formulae (2a), (2b) and (2e) are preferred.

Z is preferably a radical of the formula (3)

in which:

X is halogen such as chlorine and fluorine or a group of the formula (4)

in which $R^2$ is hydrogen, alkyl of 1 to 4 carbon atoms such as ethyl and, in particular, methyl, or alkyl of 1 to 4 carbon atoms such as, in particular, ethyl which is substituted by hydroxy, cyano, alkoxy of 1 to 4 carbon atoms such as ethoxy and methoxy, carboxy, sulfo, sulfato or phosphato, or is phenyl or naphthyl, each of which may be substituted by 1, 2 or 3 substituents from the group consisting of halogen such as chlorine and bromine, hydroxy, cyano, alkoxy of 1 to 4 carbon atoms such as ethoxy and, in particular, methoxy, alkyl of 1 to 4 carbon atoms such as ethyl and, in particular, methyl, alkoxycarbonyl of 2 to 5 carbon atoms such as ethoxycarbonyl and methoxycarbonyl, carboxy, sulfamoyl, sulfo and alkylsulfonyl having an alkyl radical of 1 to 4 carbon atoms such as methylsulfonyl and ethylsulfonyl, and of these preferably alkoxy of 1 to 4 carbon atoms, alkyl of 1 to 4 carbon atoms, carboxy and sulfo, W is alkylene of 2 to 4 carbon atoms, preferably of 2 or 3 carbon atoms, such as 1,2-ethylene and 1,3-propylene, or is alkylene of 3 to 6 carbon atoms, preferably of 4 carbon atoms, which is interrupted by 1 or 2 hetero-groups from the group consisting of the formulae —O—, —NH—, —SO$_2$—, —CO— and —N(R$^{10}$)— where R$^{10}$ is as defined above, such as, for example, groups of the formulae —(CH$_2$)$_2$—O—(CH$_2$)$_2$— and —(CH$_2$)$_2$—NH—(CH$_2$)$_2$—, or W is phenylene or naphthylene, each of which may be substituted by 1, 2 or 3 substituents from the group consisting of halogen such as chlorine and bromine, hydroxy, cyano, nitro, alkoxy of 1 to 4 carbon atoms such as ethoxy and, in particular, methoxy, alkyl of 1 to 4 carbon atoms such as ethyl and, in particular, methyl, alkoxycarbonyl of 2 to 5 carbon atoms such as ethoxycarbonyl and methoxycarbonyl, carboxy, sulfamoyl and sulfo, and of these preferably alkoxy of 1 to 4 carbon atoms, alkyl of 1 to 4 carbon atoms, carboxy and sulfo, or is phenylenealkylene or alkylenephenylene having an alkylene radical of in each case 1 to 4 carbon atoms such as, in particular, ethylene, and A is vinyl or is ethyl which is substituted in the β position by a substituent which can be eliminated under the action of alkali to form the vinyl group;

Y is chlorine, cyanoamino or a group of the formula (5)

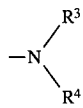
(5)

in which

R$^3$ is hydrogen, alkyl of 1 to 4 carbon atoms such as ethyl and methyl, or alkyl of 1 to 4 carbon atoms such as, in particular, ethyl which is substituted by halogen such as chlorine and bromine, hydroxy, cyano, alkoxy of 1 to 4 carbon atoms such as ethoxy and methoxy, alkoxycarbonyl of 2 to 5 carbon atoms such as ethoxycarbonyl and methoxycarbonyl, carboxy, sulfo, sulfato or phosphato, or is a group of the formula —W—SO$_2$-A where W and A are as defined above, and R$^4$ is hydrogen, alkyl of 1 to 4 carbon atoms such as ethyl and methyl, or alkyl of 1 to 4 carbon atoms such as, in particular, ethyl which is substituted by halogen such as chlorine and bromine, hydroxy, cyano, alkoxy of 1 to 4 carbon atoms such as ethoxy and methoxy, alkoxycarbonyl of 2 to 5 carbon atoms such as ethoxycarbonyl and methoxycarbonyl, carboxy, sulfo, sulfato or phosphato, or is cycloalkyl of 5 to 8 carbon atoms such as cyclohexyl, or is a group of the formula —W—SO$_2$-A where W and A are as defined above, or is phenyl or naphthyl, each of which may be substituted by 1, 2 or 3 substituents from the group consisting of halogen such as chlorine and bromine, hydroxy, cyano, alkoxy of 1 to 4 carbon atoms such as ethoxy and, in particular, methoxy, alkyl of 1 to 4 carbon atoms such as ethyl and, in particular, methyl, alkoxycarbonyl of 2 to 5 carbon atoms such as ethoxycarbonyl and methoxycarbonyl, carboxy, sulfamoyl, sulfo and alkylsulfonyl having an alkyl radical of 1 to 4 carbon atoms such as ethylsulfonyl and methylsulfonyl, or R$^3$ and R$^4$ together are an alkylene radical of 3 to 6 carbon atoms or an alkylene radical of 3 to 6 carbon atoms which is interrupted by a group —NH—, —O—, —CO—, —S—, —SO$_2$— or —N(R$^5$)— (in which R$^5$ is sulfo- or sulfato-substituted alkyl of 1 to 4 carbon atoms such as ethyl) and which together with the nitrogen atom form a heterocyclic radical such as pyrrolidino, morpholino, piperidino or piperazino.

Further preferred fiber-reactive radicals Z are those of the halo-substituted pyrimidine series, such as difluorochloropyrimidino, trichloropyrimidino, methylsulfonylchloropyrimidino and methylfluorochloropyrimidino, and furthermore the radical of dichloroquinoxaline.

In the formulae (1) to (5) and in the formulae indicated below the individual formula members, both those whose definitions are different and those whose definitions are the same within a formula, may have, within the scope of their definition, definitions which are identical to or different from one another.

Examples of alkali-eliminable substituents in the β position of the ethyl group of A are halogen atoms such as bromine and chlorine, ester groups of organic carboxylic and sulfonic acids, such as those of alkanecarboxylic acids, substituted or unsubstituted benzenecarboxylic acids and substituted or unsubstituted benzenesulfonic acids, such as the groups consisting of alkanoyloxy of 2 to 5 carbon atoms, including in particular acetyloxy, benzoyloxy, sulfobenzoyloxy, phenylsulfonyloxy and tolylsulfonyloxy, and also acid ester groups of inorganic acids, such as those of phosphoric acid, sulfuric acid and thiosulfuric acid (phosphato, sulfato and thiosulfato groups), and also dialkylamino groups having alkyl groups of in each case 1 to 4 carbon atoms such as dimethylamino and diethylamino. A is preferably β-chloroethyl or vinyl and, with particular preference, β-sulfatoethyl.

References to the groups sulfo, carboxy, thiosulfato, phosphato and sulfato include both the acid forms and the salt forms of these groups. Consequently sulfo groups are groups of the formula —SO$_3$M, carboxy groups are groups of the formula —COOM, thiosulfato groups are groups of the formula —S—SO$_3$M, phosphato groups are groups of the formula —OPO$_3$M$_2$ and sulfato groups are groups of the formula —OSO$_3$M, in which M is a hydrogen atom or an alkali metal such as sodium, potassium or lithium, or is another salt-forming metal.

R$^1$ is preferably hydrogen, methyl or ethyl, in particular hydrogen. R$^2$ is preferably hydrogen, methyl, ethyl or phenyl. Radicals of the formula (5) are preferably phenylamino which may be substituted by 1, 2 or 3, preferably 1 or 2, substituents from the group consisting of halogen such as chlorine and bromine, hydroxy, cyano, ethoxy, methoxy, methyl, ethyl, carboxy and sulfo, preferably sulfo, or are naphthylamino, preferably 2-naphthylamino, which is substituted by 1, 2 or 3 sulfo groups, or are preferably morpholino or a group of the formula (4) indicated above or a group of the formula (4a)

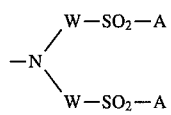
(4a)

in which W and A have the meanings given above, in particular the preferred definitions.

Aromatic radicals E of a compound of the formula H-E-NH$_2$ which is capable of coupling and can be diazotized are, for example, those of the formulae (6a), (6b) and (6c)

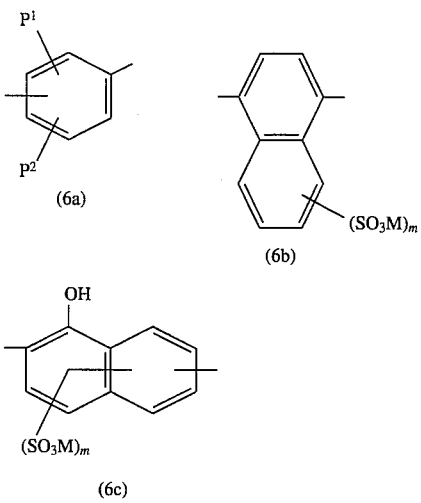

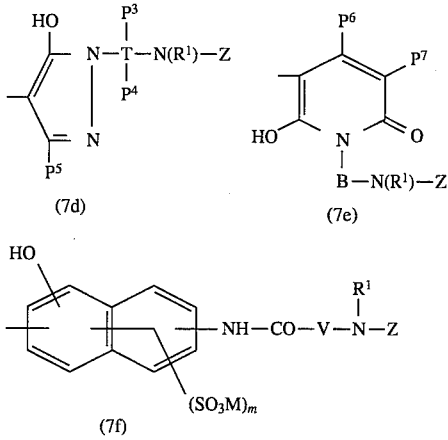

in which

M is as defined above, m is the number zero, 1 or 2 (and if m is zero the group is hydrogen), $p^1$ is hydrogen, alkyl of 1 to 4 carbon atoms such as ethyl and methyl, alkoxy of 1 to 4 carbon atoms such as ethoxy and methoxy, cyano, sulfo, carboxy, hydroxy, fluorine, chlorine, bromine or trifluoromethyl, and $p^2$ is hydrogen, alkyl of 1 to 4 carbon atoms such as methyl or ethyl, alkoxy of 1 to 4 carbon atoms such as methoxy and ethoxy, chlorine, alkanoylamino of 2 to 5 carbon atoms such as acetylamino and propionylamino, amino, benzoylamino, ureido, phenylureido, alkylureido having 1 to 4 carbon atoms in the alkyl radical, phenylsulfonyl or alkylsulfonyl of 1 to 4 carbon atoms.

Examples of radicals —K—N(R$^1$)-Z of coupling components of the formula H—K—N(R$^1$)-Z (or radicals derived therefrom of the formula H—K—N(R$^1$)H, in which the fiber-reactive Z must be introduced subsequently) are radicals of the formulae (7a) to (7f)

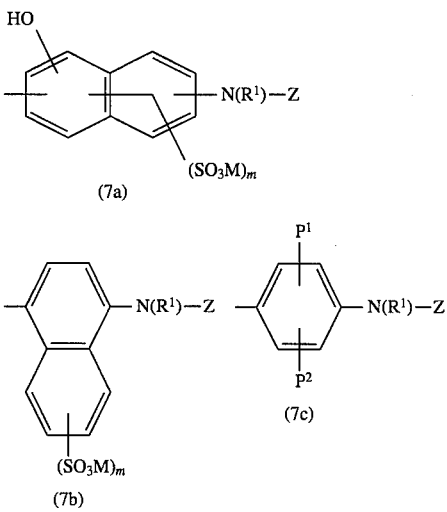

in which:

$P^1$, $P^2$, M, m, $R^1$ and Z have the meanings given above, in particular the preferred definitions;

in formula (7a) the free bond leading to the azo group is ortho to the hydroxy group on the aromatic ring system;

$P^3$ is hydrogen, alkyl of 1 to 4 carbon atoms such as ethyl and, in particular, methyl, alkoxy of 1 to 4 carbon atoms such as ethoxy and, in particular, methoxy, chlorine, bromine, fluorine, sulfo, carboxy or trifluoromethyl;

$P^4$ is hydrogen, alkyl of 1 to 4 carbon atoms such as ethyl and, in particular, methyl, alkoxy of 1 to 4 carbon atoms such as ethoxy and, in particular, methoxy, chlorine or sulfo;

$P^5$ is hydrogen, alkyl of 1 to 4 carbon atoms such as methyl, cyano, carboxy, carboalkoxy of 2 to 5 carbon atoms such as carbomethoxy and carboethoxy, carbamoyl or phenyl, preferably methyl, carboxy, methoxycarbonyl, ethoxycarbonyl or phenyl and, in particular, methyl or carboxy;

T is a benzene or naphthalene ring system, preferably a benzene ring;

$P^6$ is hydrogen or alkyl of 1 to 4 carbon atoms such as methyl, or alkyl of 1 to 4 carbon atoms which is substituted by alkoxy of 1 to 4 carbon atoms such as methoxy, or by cyano, or is phenyl, and is preferably alkyl of 1 to 4 carbon atoms or phenyl;

$P^7$ is hydrogen, chlorine, bromine, sulfo, carbamoyl, methylsulfonyl, phenylsulfonyl, cyano or sulfoalkyl of 1 to 4 carbon atoms, preferably hydrogen, sulfo, sulfoalkyl having an alkyl radical of 1 to 4 carbon atoms such as sulfomethyl, cyano or carbamoyl;

V is phenylene, preferably meta- or para-phenylene, which may be substituted by a sulfo group.

Examples of groups of the formulae (4) and (4a) are: N-[γ-(β'-chloroethylsulfonyl)propyl]amino, N-[γ-(β'-sulfatoethylsulfonyl)propyl]amino, N-[γ-(vinylsulfonyl)propyl]amino, N-[β-(β'-chloroethylsulfonyl)ethyl]amino, N-[β-(β'-sulfatoethylsulfonyl)ethyl]amino, N-[β-(vinylsulfonyl)ethyl]amino, N-methyl-N-[β-(β-chloroethylsulfonyl)ethyl]amino, N-ethyl-N-[β-(β'-chloroethylsulfonyl)propyl]amino, N-n-propyl-N-[β-(β'-chloroethylsulfonyl)ethyl]amino, N-n-butyl-N-[β-(β'-chloroethylsulfonyl)ethyl]amino, N-carboxymethyl-N-[β-(β'-bromoethylsulfonyl)ethyl]amino, N-sulfatomethyl-N-[β-(β'-chloroethylsulfonyl)ethyl]amino, N-(β-carboxyethyl)-N-[β'-(β"-chloroethylsulfonyl)ethyl]amino, N-(β-sulfatoethyl)-N-[β'-(β"-chloroethylsulfonyl)ethyl]amino, N-(β-ethoxyethyl)-N-[β' -β"-chloroethylsulfonyl)ethyl]amino, N-phenyl-N-[β-(β'- chloroethylsulfonyl)ethyl]amino, N-(4-chlorophenyl)-N-[β-(β'-chloroethylsulfonyl)ethyl]amino, N-(2-methylphenyl)-N-[β-(β'-chloroethylsulfonyl)ethyl]amino, N-(4-methoxyphenyl)-N-[β-(β'-chloroethylsulfonyl)ethyl]amino, N-(3 -sulfophenyl)-N-[β-(β'-chloroethylsulfonyl)ethyl] amino, N-( 4-sulfophenyl)-N-[β-(β'-chloroethylsulfonyl)ethyl]amino, N-(β-cyanoethyl)-N-[β'-(β"-chloroethylsulfonyl)ethyl]amino, N-phenyl-N-(β-vinylsulfonylethyl)amino, N-(4-chlorophenyl)-N-(β-vinylsulfonylethyl)amino, N-(2-methylphenyl)-N-(β-vinylsulfonylethyl)amino, N-(4-methoxyphenyl)-N-(β-vinylsulfonylethyl)amino, N-(3-sulfophenyl)-N-(β-vinylsulfonylethyl)amino, N-(4-sulfophenyl)-N-(β-vinylsulfonylethyl)amino, N-phenyl-N-[β-(β'-sulfatoethylsulfonyl)ethyl]amino, N-(4-chlorophenyl)-N-[β-(β'-sulfatoethylsulfonyl)ethyl]amino, N-(2-methylphenyl)-N-[β-(β'-sulfatoethylsulfonyl)ethyl]amino, N-(4-methoxyphenyl)-N-[β-(β'-sulfatoethylsulfonyl)ethyl] amino, N-(3 -sulfophenyl)-N-[β-(β'-sulfatoethylsulfonyl)ethyl]amino, N-(4-sulfophenyl)-N-[β-(β'-sulfatoethylsulfonyl)ethyl]amino, N-methyl-N-[γ-(β'-chloroethylsulfonyl)propyl]amino, N-ethyl-N-[γ-(β'-chloroethylsulfonyl)propyl]amino, N-n-propyl-N-[γ-(β'-chloroethylsulfonyl)propyl]amino, N-n-butyl-N-[γ-(β'-chloroethylsulfonyl)propyl]amino, N-carboxymethyl-N-[γ-(β'-bromoethylsulfonyl)propyl]amino, N-sulfatomethyl-N-[γ-(β'-chloroethylsulfonyl)propyl]-amino, N-(β-carboxyethyl)-N-[γ-(β"-chloroethylsulfonyl)propyl]amino, N-(β-sulfatoethyl)-N-[γ-(β"-chloroethylsulfonyl)propyl] amino, N-(β-sulfatoethyl)-N-[δ-(β"-chloroethylsulfonyl)butyl]amino, N-(β-ethoxyethyl)-N-[δ'-(β"-chloroethylsulfonyl)butyl]amino, N-(β-ethoxyethyl)-N-[γ'-(β"-chloroethylsulfonyl)propyl]amino, N-phenyl-N-[γ-(β'-chloroethylsulfonyl)propyl]amino, N-(4-chlorophenyl)-N-[γ-(β'-chloroethylsulfonyl)propyl]amino, N-(2-methylphenyl)-N-[γ-(β'-chloroethylsulfonyl)propyl]amino, N-(4-methoxyphenyl)-N-[γ-(β'-chloroethylsulfonyl) propyl] amino, N-(3-sulfophenyl)-N-[γ-(β'-chloroethylsulfonyl)propyl]-amino, N-(4-sulfophenyl)-N-[γ-(β'-chloroethylsulfonyl)propyl]amino, N-(β-cyanoethyl)-N-[γ'-(β"-chloroethylsulfonyl)propyl] amino, N-phenyl-N-(γ-vinylsulfonylpropyl)amino, N-(4-chlorophenyl)-N-(γ-vinylsulfonylpropyl)amino, N-(2-methylphenyl)-N-(γ-vinylsulfonylpropyl)amino, N-(4-methoxyphenyl)-N-(γ-vinylsulfonylpropyl)amino, N-(3-sulfophenyl)-N-(γ-vinylsulfonylpropyl)amino, N-(4-sulfophenyl)-N-(γ-vinylsulfonylpropyl)amino, N-phenyl-N-[γ-(β'-sulfatoethylsulfonyl)propyl]amino, N-(4-chlorophenyl)-N-[γ-(β'-sulfatoethylsulfonyl)propyl]amino, N-(2-methylphenyl)-N-[γ-(β'-sulfatoethylsulfonyl)propyl]amino, N-(4-methoxyphenyl)-N-[γ-(β'-sulfatoethylsulfonyl)propyl] amino, N-(3-sulfophenyl)-N-[γ-(β'-sulfatoethylsulfonyl)propyl]amino, N-(4 -sulfophenyl)-N-[γ-(β'-sulfatoethylsulfonyl)propyl]amino, N-phenyl-N-[α-carboxy-γ-(β'-chloroethylsulfonyl)propyl]amino, N-phenyl-N-[α-ethoxycarbonyl-γ-(β'-chloroethylsulfonyl)propyl]amino, N-phenyl-N-[α-methoxycarbonyl-γ-(β'-chloroethylsulfonyl)propyl]amino, N-phenyl-N-[β-methyl-γ-(β'-chloroethylsulfonyl)propyl]amino, N-phenyl-N-[β-ethyl-γ-(β'-chloroethylsulfonyl)propyl]amino, N-phenyl-N-[δ-(β'-chloroethylsulfonyl)butyl]amino, N-phenyl-N-[ε-(β'-chloroethylsulfonyl)pentyl]amino and N-phenyl-N-[β-(β'-chloroethylsulfonyl)hexyl]amino, bis-N,N-[γ-(β'-chloroethylsulfonyl)propyl]amino, bis-N,N-[γ(β'-sulfatoethylsulfonyl)propyl]amino, bis-N,N-[γ-(vinylsulfonyl)propyl]amino, bis-N,N-[β-(β'-chloroethylsulfonyl)ethyl]amino, bis-N,N-[β-(β'-sulfatoethylsulfonyl)ethyl]amino, bis-N,N-[β-(vinylsulfonyl)ethyl]amino, 4-(β-sulfatoethylsulfonyl)phenylamino, 3-(β-sulfatoethylsulfonyl)phenylamino, 2-methoxy-5-(β-sulfatoethylsulfonyl)phenylamino, 2,5-dimethoxy-4-(β-sulfatoethylsulfonyl)phenylamino, 2-methoxy-5-methyl-4-(β-sulfatoethylsulfonyl)phenylamino, 2-sulfo-4-(β-sulfatoethylsulfonyl)phenylamino, 2-hydroxy-5-(β-sulfatoethylsulfonyl)phenylamino, 2-bromo-5-(β-sulfatoethylsulfonyl)phenylamino, 4 -[β-(β'-sulfatoethylsulfonyl)ethyl]phenylamino, 1-sulfo-6 -(β-sulfatoethylsulfonyl)-2-naphthylamino, 8-sulfo-6-(β-sulfatoethylsulfonyl)-2-naphthylamino, 6-sulfo-8-(β-sulfatoethylsulfonyl)-2-naphthylamino, 6-(β-sulfatoethylsulfonyl)- 2-naphthylamino and 8-(β-sulfatoethylsulfonyl)- 2-naphthylamino.

Examples of further fiber-reactive radicals Z are: 2,4-dichloro-1,3,5-triazin-6-yl, 2,4-difluoro-5-chloropyrimidin- 6-yl, 2,4,5-trichloropyrimidin-6-yl, 2-methylsulfonyl-5-chloro-4-methylpyrimidin-6-yl, 4-methyl-2-fluoro-5-chloropyrimidin-6-yl, 2,3-dichloroquinoxaline-6-carbonyl and 2,4-difluoropyrimidin-6-yl, and also radicals of the formula (8a)

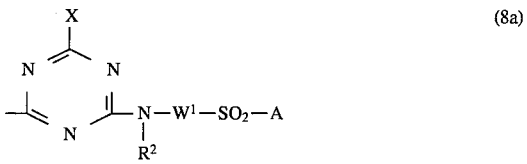

(8a)

in which X is chlorine, fluorine or cyanoamino, A has one of the meanings given above, in particular one of the preferred definitions, $R^2$ is hydrogen, ethyl, methyl, β-hydroxyethyl, β-sulfatoethyl, phenyl, 3-sulfophenyl or 4 -sulfophenyl and $W^1$ is 1,2-ethylene, 1,3-propylene, 2 -methyl-1,2-ethylene, 2-methyl-1,3-propylene, 1,4-phenylene, 1,3-phenylene, 2-methoxy-1,5-phenylene, 2,5-dimethoxy-1,4-phenylene, 2-methoxy-5-methyl- 1,4-phenylene, 2-sulfo-1,4-phenylene, 2-hydroxy-1,5-phenylene, 2-bromo-1,5-phenylene or 4-(2'-eth)phen-1,1'-ylene, in which groups position i is attached to the nitrogen atom, or is 1-sulfonaphth-2,6-ylene, 6-sulfonaphth- 2,8-ylene, naphth-2,6-ylene and naphth-2,8-ylene, in which groups position 2 is attached to the nitrogen atom, and also radicals of the formula (8b)

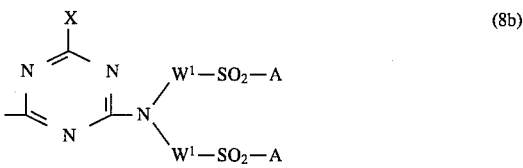

(8b)

in which X and A have one of the meanings given above, in particular one of the preferred definitions, and $W^1$ has one of the meanings given above, and is preferably 1,3-propylene or 1,2-ethylene, and also groups of the formula (8c)

(8c)

in which X is chlorine or fluorine and $Y^1$ is amino, methylamino, ethylamino, dimethylamino, diethylamino, bis-(β-hydroxyethyl)amino, β-hydroxyethylamino, phenylamino, 3-sulfophenylamino, 4-sulfophenylamino, 2-sulfophenylamino, 2,5-disulfophenylamino, 2,4-disulfophenylamino, 2-carboxyphenylamino, 4-carboxyphenylamino, 2-sulfo-4-methoxyphenylamino, 2-sulfo-4-methylphenylamino, 3-sulfo-4-methylphenylamino, 2-methylphenylamino, 3-methylphenylamino, 4-methylphenylamino, 2,5-dimethylphenylamino, 2,4-dimethylphenylamino, 2-methoxyphenylamino, 3-methoxyphenylamino, 4-methoxyphenylamino, 2- or 3- or 4-ethoxyphenylamino, N-ethylphenylamino, N-methylphenylamino, N-(β-hydroxyethyl) phenylamino, 2-chlorophenylamino, 3- or 4-chlorophenylamino, 2,5-dichlorophenylamino, 2-naphthylamino, 1-sulfo-2-naphthylamino, 3,6,8-trisulfo-2-naphthylamino, 4,6,8-trisulfo-2-naphthylamino, 4,8-disulfo-2-naphthylamino, 1,5-disulfo-2-naphthylamino, N-morpholino, N-piperidino, N-piperazino, N-pyrrolidino, N'-(β-sulfatoethyl)-N-piperazino or N'-(β-hydroxyethyl)-N-piperazino.

Among the azo compounds of the formula (1) according to the invention, particular preference is given to those of the formulae (1A), (1B), (1C), (1D), (1E), (1F), (1G) and (1H)

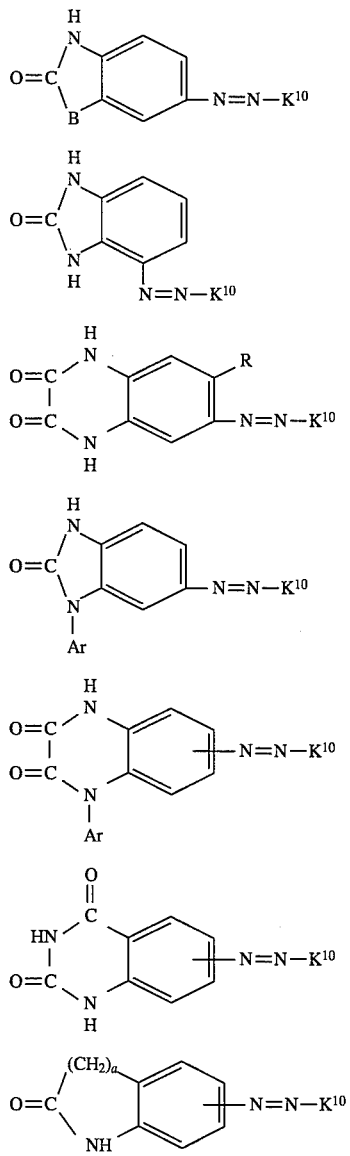

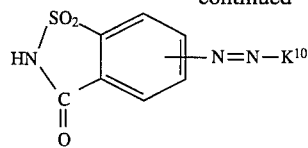

in which R is hydrogen, methyl or methoxy, B is —O— or —N($R^{10}$)— where $R^{10}$ has the meaning given above, in particular the preferred definition, a is the number 1 or 2, Ar is phenyl substituted by 1 or 2 sulfo groups, or is naphthyl substituted by 3 or preferably 2 or 3 sulfo groups, and the radical $K^{10}$ is a group of the formula (8A)

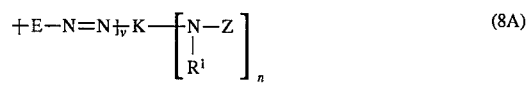

in which E, v, K, $R^1$, Z and n have one of the meanings given above, in particular one of the preferred definitions.

Of these compounds, particular emphasis is placed on those azo compounds of the formulae (9a), (9b), (9c) and (9d)

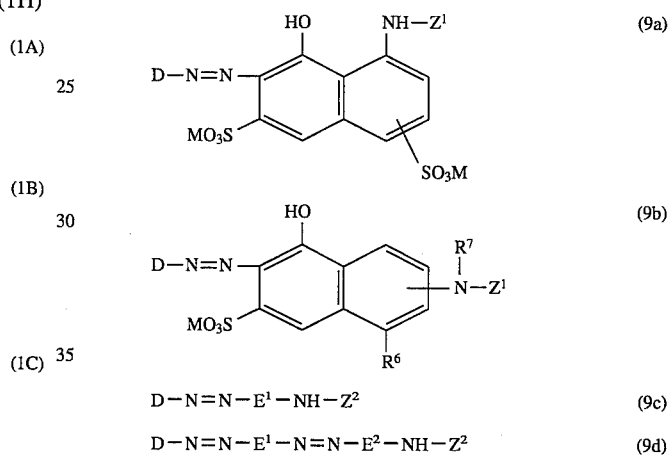

in which:

D is the radical which can be seen from the formulae (1A) to (1H) and is free from the radical —N=N—$K^{10}$;

M is as defined above;

$R^6$ is hydrogen or sulfo;

$R^7$ is hydrogen, alkyl of 1 to 4 carbon atoms such as methyl or ethyl which may be substituted by 1 or 2 substituents from the group consisting of hydroxy, sulfo, carboxy and sulfato, or is phenyl which may be substituted by 1, 2 or 3 substituents from the group consisting of sulfo and carboxy, and is preferably hydrogen;

the group —$SO_3M$ in formula (9a) is para or preferably meta to the group —N($R^7$)-$Z^1$ and in formula (9b) is ortho or meta to $R^6$;

$E^1$ is 1,4-phenylene which may be substituted by 1 or 2 substituents from the group consisting of sulfo, methyl, methoxy, ureido and acetylamino, or is 1,4-naphthylene which may be substituted by a sulfo group in position 6, 7 or 8, preferably in position 6 or 7;

$E^2$ is 1,4-phenylene which may be substituted by 1 or 2 substituents from the group consisting of sulfo, methyl, methoxy, ureido and acetylamino, or is 1,4-naphthylene which may be substituted by a sulfo group in position 6, 7 or 8, preferably in position 6 or 7;

$Z^1$ is a radical of the formula (10A) indicated and defined below, and $Z^2$ is a radical of the formula (10B) indicated and defined below

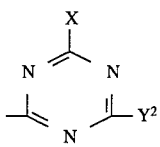
(10A)

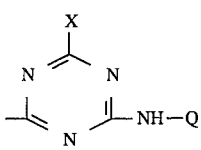
(10B)

in which

X is chlorine or fluorine, $Y^2$ is phenylamino which may be substituted by 1 or 2 sulfo groups or by a group of the formula —SO$_2$-A where A is as defined above or by 1 or 2 sulfo groups and by one of these groups —SO$_2$-A or is naphthylamino, preferably 2-naphthylamino, which may be substituted by 1, 2 or 3 sulfo groups or by a group of the formula —SO$_2$-A where A is as defined above or by 1 or 2 sulfo groups and by this group —SO$_2$-A, or is a group of the formula (11a), (11b) or (11c)

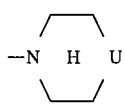
(11a)

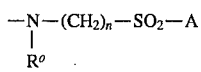
(11b)

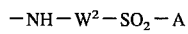
(11c)

in which

U is —O—, —S—, —SO$_2$— or —NH— or is a group of the formula

in which $R^A$ is hydrogen, β-hydroxyethyl or β-sulfatoethyl, n is the number 2, 3 or 4, preferably 2 or 3, A is as defined above, $R^o$ is hydrogen, methyl, ethyl, phenyl, monosulfophenyl, disulfophenyl or a radical of the formula —(CH$_2$)$_n$—SO$_2$-A where n and A are as defined above, $W^2$ is alkylene of 3 to 6 carbon atoms, preferably of 4 carbon atoms, which is interrupted by 1 or 2 hetero groups from the group consisting of the formulae —O—, —NH—, —SO$_2$— and —CO—, such as for example a group of the formula —(CH$_2$)$_2$—O—(CH$_2$)$_2$— or —(CH$_2$)$_2$—NH—(CH$_2$)$_2$—, and Q is phenyl which may be substituted by 1, 2 or 3 sulfo groups or by a group of the formula —SO$_2$-A where A is as defined above or by 1 or 2 sulfo groups, preferably 1 sulfo group, and by this group —SO$_2$-A, or is naphthyl, preferably 2-naphthyl, which may be substituted by 1, 2 or 3 sulfo groups or by 1 group of the formula —SO$_2$-A where A is as defined above or by 1 or 2 sulfo groups and by this group —SO$_2$-A.

Y is preferably morpholino, monosulfophenylamino, disulfophenylamino, monosulfophenylamino which is substituted by methoxy, methyl, carboxy, sulfo, hydroxy, chlorine or bromine, a group of the formula (11c) as defined above or a group of the formula (11b) in which n and A are as defined above and $R^o$ is phenyl or monosulfophenyl or in which $R^o$ is a radical of the formula —(CH$_2$)$_n$—SO$_2$-A where n and A are as defined above.

The present invention relates furthermore to processes for the preparation of the azo compounds of the formula (1) according to the invention, which comprise diazotizing a compound of the formula (12)

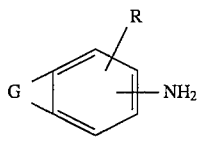
(12)

in which R and G have one of the meanings given above, in particular one of the preferred definitions, and coupling the diazotization product with a compound of the formula (13)

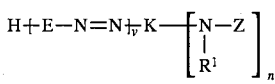
(13)

in which E, v, K, $R^1$, Z and n have one of the meanings given above, in particular one of the preferred definitions, or comprise diazotizing a compound of the formula (14)

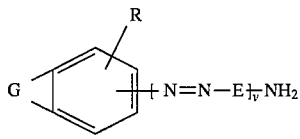
(14)

where G, R, E and v have one of the meanings given above, in particular one of the preferred definitions, and coupling the diazotization product with a compound of the formula H—K-Z where K and Z are as defined above, or comprise reacting a compound of the formula (15)

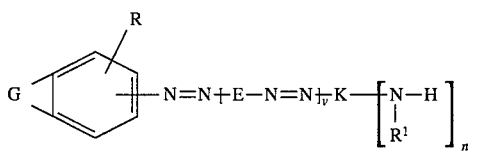
(15)

in which G, R, v, K, $R^1$ and n have one of the meanings given above, in particular one of the preferred definitions, with a compound of the formula $X^o$-Z in which $X^o$ is chlorine, bromine or fluorine and Z is as defined above, and of these preferably with a compound of the formula (16)

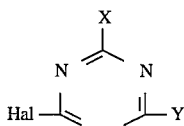
(16)

in which X and Y have the meanings given above, in particular the preferred definitions, and Hal is chlorine or fluorine.

The diazotization reactions are carried out by a procedure which is known per se in an aqueous medium at a pH of less than 2 and at a temperature of between −5° C. and 15° C. The coupling reactions are also carried out by a procedure which is known per se in an aqueous solution or in an aqueous-organic medium at a pH of between 4 and 9, preferably between 5 and 7, and at a temperature of between 0° C. and 40° C., preferably between 5° C. and 25° C.

The condensation reactions between the compounds of the formula (15) and the fiber-reactive starting compound of the formula $X^o$-Z where $X^o$ and Z are as defined above, such as preferably of the formula (16) indicated and defined above, are likewise carried out in an aqueous or aqueous-organic medium in suspension or solution. If these reactions are carried out in an aqueous-organic medium, then the organic medium is, for example, acetone, dimethylformamide, dimethyl sulfoxide or N-methylpyrrolidone. Advantageously, the hydrogen halide which is liberated during the reaction is neutralized continuously by addition of aqueous alkali metal or alkaline earth metal hydroxides, carbonates or bicarbonates. The reaction is generally carried out at a temperature of between −5° C. and +95° C. and at a pH of between 3 and 11, preferably between 4 and 6, and in the case where $X^o$ and/or Hal is fluorine, preferably at a temperature of between 20° and 40° C. and at a pH of between 4 and 10, particularly preferably between 4 and 7.

The starting compounds of the formula (12) are known from the literature (see for example Dyes and Pigments 21 (1993), 123, and Ann. Chim. 49 (1959), 1809); insofar as individual compounds are not described, they can be prepared by analogy with the procedure of the prior art. For example, compounds of the formula (12) in which G is a radical of the formula (2a) or (2e) where $R^{10}$ has one of the given meanings other than hydrogen can be prepared by starting from compounds of the formula (a) given below where $R^{10}$ is as defined above (which are known, for example, from Fierz-David & Blangley, "Farbenchemic" [Color Chemistry], 8th Edition (1952), Springer Verlag, Table 5 of the appendix) and reacting these compounds with phosgene, dialkyl carbonate or alkyl chloroformates or with oxalyl chloride at a temperature of between 0° and 100° C. and at a pH of between 6 and 10, and, in the resulting heterocyclic compound of the formula (b)

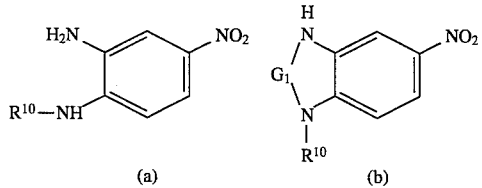

(a)          (b)

in which $R^{10}$ is as defined above and $G_1$ is the group —CO— or —CO—CO—, reducing the nitro group to the amino group, as known in the art, for example, using hydrogen and a nickel, palladium or platinum catalyst.

The remaining starting compounds, such as the compounds of the formulae H-E-$NH_2$ and H—K—N($R^1$)H and the fiber-reactive starting compounds of the formula $X^o$-Z, are described abundantly in the literature and are widely employed for the preparation of fiber-reactive dyes (see for example the European Patent Application Publications Nos. 0,541,057, 0,542,214 and 0,548,795) or can be prepared by analogy with the procedures indicated therein using appropriate starting compounds.

Examples of starting compounds of the formula (12) are 4-aminobenzimidazolin-2-one, 5-aminobenzimidazolin-2-one, 1-N-(4'-sulfophenyl)-5-aminobenzimidazolin-2-one, 1-N-(3'-sulfophenyl)-5-aminobenzimidazolin-2-one, 1-N-(6',8'-disulfo-2'-naphthyl)-5-aminobenzimidazolin-2-one, 6-aminoquinoxaline-2,3-dione, 7-methyl-6-aminoquinoxaline-2,3-dione, 7-methoxy-6-aminoquinoxaline-2,3-dione, 7-ethoxy-6-aminoquinoxaline-2,3-dione, 4-N-(4'-sulfophenyl)-6-aminoquinoxaline-2,3-dione, 4-N-(3'-sulfophenyl)-6-aminoquinoxaline-2,3-dione, 4-N-(2',5'-disulfophenyl)-6-aminoquinoxaline-1,3-dione, 4-N-(6',8'-disulfo-2'-naphthyl)-6-aminoquinoxaline-2,3-dione, 4-N-(4',6',8'-trisulfo-2'-naphthyl)-6-aminoquinoxaline-2,3-dione, 5-aminooxazolin-2-one, 6-chloro-5-aminooxazolin-2-one, 6-aminoquinazoline-2,4-dione, 7-aminoquinazoline-2,4-dione, 7-amino-3,4-dihydroquinolin-2-one, 6-amino-1,3-dihydroindol-2-one, 5-amino-1,2-benzisothiazolin-3-one 1,1-dioxide, 6-amino-1,2-benzisothiazolin-3-one 1,1-dioxide, 5-aminophthalimide, 5-amino-N'-(4'-sulfophenyl)phthalimide, 5-amino-N'-(3'-sulfophenyl)phthalimide, 5-amino-N'-(5',7'-disulfo-2'-naphthyl)phthalimide and 5-amino-N'-(6',8'-disulfo-2'-naphthyl)phthalimide.

Some of the starting compounds of-the formula (17)

where $R^2$ W and A are as defined above, which are present as amino radicals in the starting compounds of the formulae (13) and (16) and are used for their synthesis, are known, for example, from European Patent Application Publications Nos. 0,070,806, 0,070,807, 0,374,758, 0,499,588, 0,541,057 and 0,568,860 and from U.S. Pat. Nos. 4,908,436 and 5,138,041 and from British Patent 1,576,237. The amino compounds of the formula (17) in which $R^2$ is a substituted or unsubstituted phenyl radical and W is the 1,3-propylene radical, in contrast, have not hitherto been described per se. They can be prepared, for example by reacting N-allyl-N-acetylaniline (see J. Org. Chem. 14, 1099 (1949)) with 2-mercaptoethanol in the presence of a free-radical initiator by analogy with the procedure described in German Offenlegungsschrift No. 41 06 106, oxidizing the resulting N-[γ-(β'-hydroxyethylthio)propyl]-N-acetylaniline compound to give the sulfonyl compound, for example using hydrogen peroxide in the presence of a catalytic quantity of a transition metal compound such as, for example, tungsten oxide. The acetyl group is cleaved off from the resulting sulfonyl compound by hydrolysis in the alkaline or acid ravage, preferably in an aqueous solution containing hydrochloric acid, such as, for example, in from 5 to 30% strength aqueous hydrochloric acid, at a temperature of between 80° and 100° C.

The N-phenyl-N-[γ-(β'-hydroxyethylsulfonyl)propyl]amine obtained in this way can be separated off from the aqueous phase of the aqueous synthesis solution which has been rendered neutral. The β-hydroxyethylsulfonyl group of this compound can be esterified by customary methods, for example conversion using concentrated sulfuric acid at a temperature of between 10° and 30° C., to give the β-sulfatoethylsulfonyl compound, or with thionyl chloride or gaseous hydrogen chloride to give the β-chloroethylsulfonyl compound.

Examples of starting compounds of the formula (17) are N-[γ-(β'-chloroethylsulfonyl)propyl]amine, N-[γ-(β'-sulfatoethylsulfonyl)propyl]amine, N-[γ-(vinylsulfonyl)propyl]amine, N-[β-(β'-chloroethylsulfonyl)ethyl]amine, N-[β-(β'-sulfatoethylsulfonyl)ethyl]amine, N-[β-(vinylsulfonyl)ethyl]amine, N-methyl-N-[β-(β'-chloroethylsulfonyl)ethyl]amine, N-ethyl-N-[β-(β'-chloroethylsulfonyl)propyl]amine, N-n-propyl-N-[β-(β'-chloroethylsulfonyl)ethyl]amine, N-n-butyl-N-[β-(β'-chloroethylsulfonyl)ethyl]amine, N-carboxymethyl-N-[β-(β'-bromoethylsulfonyl)ethyl]amine, N-sulfatomethyl-N-[β-(β'-chloroethylsulfonyl)ethyl]amine, N-(β-carboxyethyl)-N-[β'-(β''-chloroethylsulfonyl)ethyl]amine, N-(β-sulfatoethyl)-N-[β'-(β''-chloroethylsulfonyl)ethyl]amine, N-(β-ethoxyethyl)-N-[β'-(β''-chloroethylsulfonyl)ethyl]amine, N-phenyl-N-[β-(β'-chloroethylsulfonyl)ethyl]amine, N-(4-chlorophenyl)-N-[β-(β'-chloroethylsulfonyl)ethyl]

amine, N-(2-methylphenyl)-N-[β-(β'-chloroethylsulfonyl)ethyl]-amine, N-(4-methoxyphenyl)-N-[β-(β'-chloroethylsulfonyl)ethyl]amine, N-(3-sulfophenyl)-N-[β-(β'-chloroethylsulfonyl)ethyl]amine, N-(4-sulfophenyl)-N-[β-(β'-chloroethylsulfonyl)ethyl]amine, N-(β-cyanoethyl)-N-[β'-(β''-chloroethylsulfonyl)ethyl]amine, N-phenyl-N-(β-vinylsulfonylethyl)amine, N-(4-chlorophenyl)-N-(β-vinylsulfonylethyl)amine, N-(2-methylphenyl)-N-(β-vinylsulfonylethyl)amine, N-(4-methoxyphenyl)-N-(β-vinylsulfonylethyl)amine, N-(3-sulfophenyl)-N-(β-vinylsulfonylethyl)amine, N-(4-sulfophenyl)-N-(β-vinylsulfonylethyl) amine, N-phenyl-N-[β-(β'-sulfatoethylsulfonyl)ethyl]amine, N-(4-chlorophenyl)-N-[β-(β'-sulfatoethylsulfonyl)ethyl]amine, N-(2-methylphenyl)-N-[β-(β'-sulfatoethylsulfonyl)ethyl]amine, N-(4-methoxyphenyl)-N-[β-(β'-sulfatoethylsulfonyl)ethyl]amine, N-(3-sulfophenyl)-N-[β-(β'-sulfatoethylsulfonyl)ethyl]amine, N-(4-sulfophenyl)-N-[β-(β'-sulfatoethyl)ethyl]amine, N-methyl-N-[γ-(β'-chloroethylsulfonyl)propyl]amine, N-ethyl-N-[γ-(β'-chloroethylsulfonyl)propyl]amine, N-n-propyl-N-[γ-(β'-chloroethylsulfonyl)propyl]amine, N-n-butyl-N-[γ-(β'-chloroethylsulfonyl)propyl]amine, N-carboxymethyl-N-[γ-(β'-bromoethylsulfonyl)propyl]amine, N-sulfatomethyl-N-[γ-(β'-chloroethylsulfonyl)propyl]amine, N-(β-carboxyethyl)-N-[γ-(β''-chloroethylsulfonyl)propyl]amine, N-(β-sulfatoethyl)-N-[γ-(β''-chloroethylsulfonyl)propyl]amine, N-(β-sulfatoethyl)-N-[δ'-(β''-chloroethylsulfonyl)butyl]amine, N-(β-ethoxyethyl)-N-[δ'-(β''-chloroethylsulfonyl)butyl]amine, N-(β-ethoxyethyl)-N-[γ'-(β''-chloroethylsulfonyl)propyl]amine, N-phenyl-N-[γ-(β'-chloroethylsulfonyl)propyl]amine, N-(4-chlorophenyl)-N-[γ-(β'-chloroethylsulfonyl)propyl]amine, N-(2-methylphenyl)-N-[γ-(β'-chloroethylsulfonyl)propyl]amine, N-(4-methoxyphenyl)-N-[γ-(β'-chloroethylsulfonyl)propyl]amine, N-(3-sulfophenyl)-N-(β'-chloroethylsulfonyl)propyl]amine, N-(4-sulfophenyl)-N-[γ-(β'-chloroethylsulfonyl)propyl]amine, N-(β-cyanoethyl)-N-[γ'-(β''-chloroethylsulfonyl)propyl]amine, N-phenyl-N-(γ-vinylsulfonylpropyl)amine, N-(4-chlorophenyl)-N-(γ-vinylsulfonylpropyl)amine, N-(2-methylphenyl)-N-(γ-vinylsulfonylpropyl)amine, N-(4-methoxyphenyl)-N-(γ-vinylsulfonylpropyl)amine, N-(3-sulfophenyl)-N-(γ-vinylsulfonylpropyl)amine, N-(4-sulfophenyl)-N-(γ-vinylsulfonylpropyl)amine, N-phenyl-N-(β'-sulfatoethylsulfonyl)propyl]amine, N-(4-chlorophenyl)-N-[γ-(β'-sulfatoethylsulfonyl)propyl]amine, N-(2-methylphenyl)-N-[γ-(β'-sulfatoethylsulfonyl)propyl]amine, N-(4-methoxyphenyl)-N-[γ-(β'-sulfatoethylsulfonyl)propyl]amine, N-(3-sulfophenyl)-N-[γ-(β'-sulfatoethylsulfonyl)propyl]amine, N-(4-sulfophenyl)-N-[γ-(β'-sulfatoethylsulfonyl)propyl]amine, N-phenyl-N-[α-carboxy-γ-(β''-chloroethylsulfonyl)propyl]amine, N-phenyl-N-[α-ethoxycarbonyl-γ-(β'-chloroethylsulfonyl)propyl]amine, N-phenyl-N-[β-methoxycarbonyl-γ-(β'-chloroethylsulfonyl)propyl]amine, N-phenyl-N-[β-methyl-γ-(β'-chloroethylsulfonyl)propyl]amine, N-phenyl-N-[β-ethyl-γ-(β'-chloroethylsulfonyl)propyl]amine, N-phenyl-N-[δ-(β'-chloroethylsulfonyl)butyl]amine, N-phenyl-N-[ε-(β'-chloroethylsulfonyl)pentyl]amine, N-phenyl-N-[β-(β'-chloroethylsulfonyl)hexyl]amine, 3- and 4-(β-sulfatoethylsulfonyl)aniline, 2-methoxy-5-(β-sulfatoethylsulfonyl)aniline, 2,5-dimethoxy-4-(β-sulfatoethylsulfonyl) aniline, 2-methoxy-5-methyl-4-(β-sulfatoethylsulfonyl)aniline, 2-sulfo-4-(β-sulfatoethylsulfonyl)aniline, 2-hydroxy- and 2-bromo-5-(β-sulfatoethylsulfonyl)aniline, 4-[β-(β'-sulfatoethylsulfonyl)ethyl]aniline, 1-sulfo-6-(β-sulfatoethylsulfonyl)- 2-naphthylamine, 8-sulfo-6-(β-sulfatoethylsulfonyl)- 2-naphthylamine, 6-sulfo-8-(β-sulfatoethylsulfonyl)- 2-naphthylamine and 8- and 6-(β-sulfatoethylsulfonyl)- 2-naphthylamine.

Examples of starting compounds which are used for the preparation of disazo and trisazo compounds of the formula (1) according to the invention, initially as coupling component and then, in the form of the resulting amino-azo compound, as diazo component, which are of the general formula H-E-NH$_2$, are aniline, 3-methylaniline, 2-methoxy-5-methylaniline, 2,5-dimethylaniline, 3-ureidoaniline, 3-acetylaminoaniline, 3-propionylaminoaniline, 3-butyrylaminoaniline, 3-methoxyaniline, 2-methyl-5-acetylaminoaniline, 2-methoxy-5-acetylaminoaniline, 2-methoxy-5-methylaniline, 3-(hydroxyacetylamino)aniline, 1,3-diaminobenzene, 1,3-diaminobenzene-4-sulfonic acid, 2- and 3-sulfoaniline, 3-hydroxyaniline, 1-aminonaphthalene-6-, -7- or -8-sulfonic acid, 1-amino-2-methoxynaphthalene-6-sulfonic acid, 2-amino-5-hydroxynaphthalene- 7-sulfonic acid, 2-amino-5-hydroxynaphthalene-1,7-disulfonic acid, 2-amino-8-hydroxynaphthalene-6-sulfonic acid, 2-(4'-aminobenzoylamino)-5-naphthol-7-sulfonic acid, 1-(4'-amino-2'-sulfophenyl)-3-methyl-5-pyrazolone, 1-(4'-amino-2'-sulfophenyl)-3-carboxy-5-pyrazolone and N-(acetoacetyl)-3-sulfo-4-aminoanilide.

Examples of coupling components of the formula H—K—N(R$^1$)H which can be used for synthesizing the azo compounds according to the invention and in whose amino groups the radical of the fiber-reactive group can be introduced are aniline, 3-methylaniline, 2,5-dimethylaniline, 2,5-dimethoxyaniline, 3-methoxyaniline, 3-acetylaminoaniline, 3-propionylaminoaniline, 3-butyrylaminoaniline, 3-benzoylaminoaniline, 3-(hydroxyacetylamino)aniline, 3-ureidoaniline, 2-methyl-5-acetylaminoaniline, 2-methoxy-5-acetylaminoaniline, 2-methoxy-5-methylaniline, 1-aminonaphthalene-6-sulfonic acid, 1-aminonaphthalene-7-sulfonic acid, 4-sulfo-1,3-diaminobenzene, 6-sulfo-2-methoxy-1-aminonaphthalene, 5,7-disulfo-2-aminonaphthalene, 1-amino-8-hydroxynaphthalene-4-sulfonic acid, 1-amino-8-hydroxynaphthalene-6-sulfonic acid, 1-amino-8-hydroxynaphthalene-2,4-disulfonic acid, 1-amino-8-naphthol- 3,6-disulfonic acid, 1-amino-8-hydroxy-4,6-disulfonic acid, 1-amino-8-hydroxynaphthalene-2,4,6-trisulfonic acid, 2-(methylamino)- and 2-(ethylamino)-5-hydroxynaphthalene-7-sulfonic acid, 2-amino-5-hydroxynaphthalene- 1,7-disulfonic acid, 2-(methylamino)- and 2-(ethylamino)-8-hydroxynaphthalene-6-sulfonic acid, 2-amino-8-hydroxynaphthalene-3,6-disulfonic acid, 2-(4'-amino-3'-sulfophenylamino)-5-hydroxynaphthalene-7-sulfonic acid, 1-amino-8-hydroxy-2-(phenylazo)-naphthalene-3,6-disulfonic acid, 1-amino-8-hydroxy-2-(4'-sulfophenylazo)naphthalene- 3,6-disulfonic acid, 1-amino-8-hydroxy-2-(2',5'-disulfophenylazo)naphthalene-3,6-disulfonic acid, 1-(β-aminoethyl)-3-cyano-4-methyl-6-hydroxy-2-pyridone, 1-(β-aminopropyl)-3-sulfomethyl-4-methyl-6-hydroxy-2-pyridone, 1,3-diaminobenzene, 3-[N,N-di-(β-hydroxyethyl)]aminoaniline, 3-[N,N-di-(β-sulfatoethyl)]-amino-4-methoxyaniline, 3-(sulfobenzylamino)aniline, 3-(sulfobenzoylamino)- 4-chloroaniline and 3-[N,N-di-(sulfobenzyl)]aminoaniline, 2-sulfo-5-acetylaminoaniline, 2-amino-5-naphthol-7-sulfonic acid, 2-amino-8-naphthol-6-sulfonic acid, 1-(4'-aminobenzoyl)amino-8-hydroxynaphthalene-3,6-disulfonic acid, 1-(4'-aminobenzoyl)amino-8-hydroxynaphthalene-4,6-disulfonic acid, 1-(3'-aminobenzyl)amino- 8-hydroxynaphthalene-3,6-disulfonic acid, 1-(3'-aminobenzoyl)amino-8-hydroxynaphthalene-4,6-disulfonic acid, 1-(2'-aminobenzoyl)amino-8-hydroxynaphthalene- 3,6-disulfonic acid, 1-(2'-aminobenzoyl)amino-8-hydroxynaphthalene-4,6-disulfonic acid, 2-(3'-aminobenzoyl)amino- 5-hydroxynaphthalene-7-sulfonic acid, 2-(2'-aminobenzoyl)amino-5-hydroxynaphthalene-7-sulfonic acid, 2-(4'-aminobenzoyl)amino-8-hydroxynaphthalene-6 -sulfonic acid, 2-(3'-aminobenzoyl)amino-8-hydroxynaphthalene- 6-sulfonic acid, 2-(2'-aminobenzoyl)amino-8-hydroxynaphthalene-6-sulfonic acid, 2-(4'-aminobenzoyl)amino-5-naphthol-7-sulfonic acid, 1-(4'-amino- or 1-(4'-acetylamino-2-sulfophenyl)-3-methyl- or -3-carboxy-5-pyrazolone, N-(3-sulfo-4-amino)acetoacetylanilide, (1-(3'-aminobenzoyl)- or 1-(4'-aminobenzoyl)amino-8-naphthol-3,6- or -4,6-disulfonic acid, 1-acetylamino-8-naphthol-3,6- or -4,6-disulfonic acid, 2-acetylamino-5-naphthol-7-sulfonic acid, 2-acetylamino-8-naphthol-6-sulfonic acid, 3-acetylamino-8-naphthol-6-sulfonic acid, 3-(N-methylamino)-8-naphthol-6-sulfonic acid, 1-(3'-amino- or 1-(3'-acetylamino-6'-sulfophenyl)-3-methyl- or -3-carboxy-5-pyrazolone, 2-(N-methyl-N-acetylamino)- or 2-methylamino-5-naphthol-7-sulfonic acid, N-methylaniline and N-propyl-m-toluidine.

The separation of the azo compounds of the formula (1) prepared in accordance with the invention from the synthesis mixtures is carried out by generally known methods, either by precipitation from the reaction medium by means of electrolytes such as, for example, sodium chloride or potassium chloride, or by concentration of the reaction solution by evaporation, for example by spray drying, it being possible to add a buffer substance to this reaction solution.

The azo compounds of the formula (1)—referred to below as dyes (1)—are suitable for the dyeing and printing of a wide variety of materials such as silk, leather, wool, nylon fibers and polyurethanes, and in particular of cellulose-containing fiber materials of all kinds. Examples of such fiber materials are natural cellulose fibers such as cotton, linen and hemp, and also rayon and regenerated cellulose. The dyes (1) are also suitable for the dyeing or printing of fibers containing hydroxy groups and present in blend fabrics, for example blends of cotton with polyester fibers or nylon fibers.

The dyes (1) can be applied to the fiber material and fixed on the fibers in a variety of ways, in particular in the form of aqueous dye solutions and printing pastes. They are suitable both for the exhaust process and for dyeing by the padding process, in which the goods are impregnated with aqueous solutions of dye which may contain salt and the dye is fixed by treatment with alkali or in the presence of alkali, with or without the action of heat. The dyes according to the invention are particularly suitable for the so-called pad-batch process, in which the dye is applied to the padder together with the alkali and is then fixed by storage for a number of hours at room temperature. After the fixing operation the dyes or prints are rinsed thoroughly with cold and hot water, with the addition if desired of an agent which has a dispersing action and which promotes the diffusion of the unfixed portions. These dyeing and printing processes are described abundantly in the general technical literature as well as in the patent literature, for example in the documents mentioned at the outset.

The present invention therefore also relates to the use of the dyes (1) for the dyeing (including printing) of these materials and to processes for the dyeing (and printing) of such materials by a customary procedure, in which processes a dye (1) is employed as colorant, by applying the dye (1) in an aqueous medium to the material and fixing the dye on the material by means of heat or by means of an alkaline compound or by both means.

The dyes (1) are distinguished by high reactivity, good fixation and a very good build-up behavior. They can therefore be applied by the exhaust dyeing process at low dyeing temperatures, and require only short steaming times in the pad-steam process. The degrees of fixation are high, and the unfixed portions can readily be washed out, with a notably small difference between the degree of exhaustion and the degree of fixation, i.e. the loss on soaping is very low. The dyes (1) are also particularly suitable for printing, especially on cotton, but also for the printing of nitrogen-containing fibers, for example of wool or silk, or of blend fabrics containing wool or silk.

The dyes (1) are also particularly suitable for low-salt exhaust dyeing processes in which the dyeing liquor contains a total of from 20 to 40 g/l (rather than the 50 to 80 g/l customary in the art) of one or more electrolyte salts such as sodium chloride, potassium chloride and sodium sulfate. Despite this low concentration of electrolyte salt in the exhaust dyeing liquor, the dyes (1) exhaust onto the fibre material uniformly and in a high color strength, thus giving level and strong dyeings. The high levelness of the dyeings in low-salt dyeing is retained even if light shades are desired and the dyes (1) are consequently only used in small quantities in the dyeing liquor. The possibility of low-salt dyeing with the dyes (1) results in a technical advantage, especially from the ecological viewpoint.

The dyeings and prints produced using the dyes (1) possess, especially on cellulosic fiber materials, a high color strength and a high fiber-dye bond stability, both in the acid and in the alkaline range, as well as a good light fastness and very good wet fastness properties, such as fastnesses to washing, water, salt water, cross-dyeing and perspiration, and also good fastness to dry heat setting, to ironing and to crocking.

The Examples which follow serve to illustrate the invention. Parts and percentages are by weight unless otherwise noted. The relationship between parts by weight and parts by volume is that of the kilogram to the liter.

The compounds described by way of formulae in the Examples are given in the form of the free acid; they are generally prepared and isolated in the form of their alkali metal salts, such as the lithium, sodium or potassium salts, and are used for dyeing in the form of their salts. Similarly, the starting compounds and components mentioned in the subsequent Examples, especially the Tabular Examples, in the form of the free acid can be employed in the synthesis as such or in the form of their salts, preferably the alkali metal salts.

The absorption maxima ($\lambda_{max}$) indicated for the dyes according to the invention in the visible region were determined using their alkali metal salts in aqueous solution. In the Tabular Examples the $k_{max}$ values are given in brackets where the shade is stated: the wavelength indicated is in nm.

EXAMPLE 1 a) 50.6 parts of aniline-2,5-disulfonic acid are added over the course of about 60 minutes to a suspension of 37.6 parts of cyanuric chloride in 2000 parts of water at a temperature of between 0° and 3° C. and at a pH of between 2 and 2.5. The mixture is subsequently stirred for about 30 minutes and then an aqueous suspension of 50 parts of 3-amino-8-hydroxy-6-sulfonaphthalene in 1000 parts of water is added, and the mixture is adjusted to a pH of 4.5, heated to 40° C. and stirred while maintaining these conditions for about two hours more.

19 b) 60 parts of 31% strength aqueous hydrochloric acid and 14 parts of sodium nitrite are added with thorough stirring to 29.8 parts of 5-aminobenzimidazolin-2-one in 3000 parts of water at from 0° to 5° C. The batch is subsequently stirred for about 30 minutes at this temperature, after which the resulting diazonium salt solution is added over the course of about 15 minutes, while maintaining a pH of between 6 and 7, to the solution prepared in a) of the compound 3-N-[2'-(2",5"-disulfophenyl)amino-4'-chloro-1',3',5'-triazin-6'-yl]-amino-8-hydroxy-6-sulfonaphthalene used as coupling component. The mixture is subsequently stirred for about 12 hours while maintaining this pH and at a temperature of between 20° and 25° C. after which the resulting azo compound according to the invention which, written in the form of the free acid, has the formula

20 subsequently stirred for about 12 hours while maintaining a pH of 7 and at a temperature of between 20° and 25° C.

The azo compound according to the invention which, written in the form of the free acid, has the formula

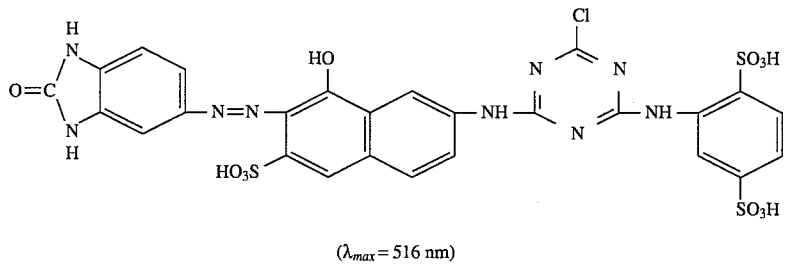

($\lambda_{max}$ = 516 nm)

is isolated as an alkali metal salt (sodium salt) in a customary manner, for example by salting out with sodium chloride.

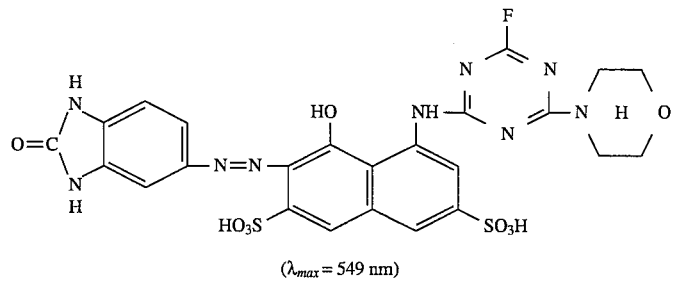

($\lambda_{max}$ = 549 nm)

The monoazo compound according to the invention displays very good fiber-reactive dye properties and gives strong red dyeings and prints having good fastness properties when applied to the fiber materials mentioned in the description, especially to cellulosic fiber materials such as cotton, by the dyeing and printing processes which are customary in the art for fiber-reactive dyes.

EXAMPLE 2

30 parts of 31% strength aqueous hydrochloric acid and 6.9 parts of sodium nitrite are added with thorough stirring to 14.9 parts of 5-aminobenzimidazolin-2-one in 600 parts of water at a temperature of between 0° and 5° C. The mixture is subsequently stirred at this temperature for 30 minutes and the resulting diazonium salt solution is then added over the course of 15 minutes to a solution of 54.5 parts of 1-N-(2'-morpholino-4'-fluoro-1',3',5'-triazin-6'-yl)amino-8-hydroxy-3,6-disulfonaphthalene (prepared according to European Patent Application Publication No. 0,542,082) in 1000 parts of water, and the mixture is is isolated from the synthesis solution as an alkali metal salt (sodium salt) in a customary manner, for example by salting out with sodium chloride.

It displays very good fiber-reactive dye properties and dyes cellulosic fiber materials, for example, in strong, brilliant violet shades with a high degree of fixation by the customary application methods.

EXAMPLE 3

30 parts of 4-aminobenzimidazolin-2-one are diazotized in a mixture of 3000 parts of water and 60 parts of 31% strength aqueous hydrochloric acid at a temperature of from 0° to 5° C. by addition of 14 parts of sodium nitrite. The mixture is subsequently stirred for about 30 minutes and the resulting diazonium salt solution is added, while maintaining a pH of from 6 to 7, over the course of about 15 minutes to the solution of the coupling component prepared according to Example 1a). The coupling reaction is brought to completion within this pH range, with additional stirring at from 20° to 25° C., for about 12 hours, after which the azo compound according to the invention of the following formula (written in the form of the free acid)

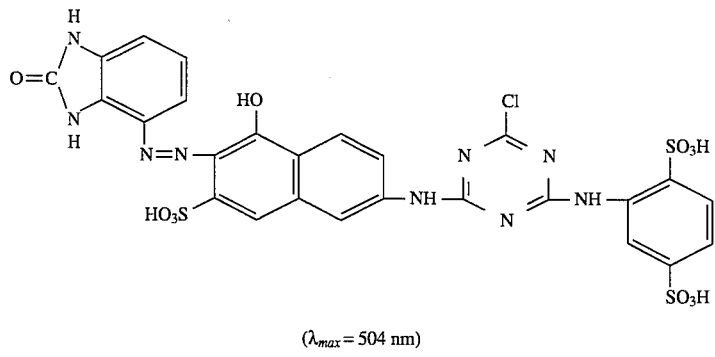

($\lambda_{max}$ = 504 nm)

is isolated as an alkali metal salt (sodium salt) in a customary manner, for example by spray-drying of the aqueous synthesis solution or by salting out the compound from the synthesis solution using sodium chloride.

The azo compound according to the invention displays very good fiber-reactive dye properties and dyes the materials mentioned in the description, especially cellulose-containing fiber materials such as cotton, in strong, reddish brown shades with good fastness properties by the application processes which are customary in the art for fiber-reactive dyes.

EXAMPLE 4

14.9 parts of 4-aminobenzimidazolin-2-one are diazotized in aqueous hydrochloric acid solution (600 parts of water and 30 parts of aqueous 31% strength hydrochloric acid) at from 0° to 5° C. using 6.9 parts of sodium nitrite. The mixture is subsequently stirred for 30 minutes at from 0° to 5° C. after adding the sodium nitrite, and the resulting diazonium salt solution is then added to the coupling component prepared according to the indications of Example 2. The reaction mixture is subsequently stirred for about 12 hours, while maintaining a pH of about 7 and a temperature of from 20° to 25° C., after which the azo compound according to the invention is isolated in a customary manner.

Written in the form of the free acid, it has the formula

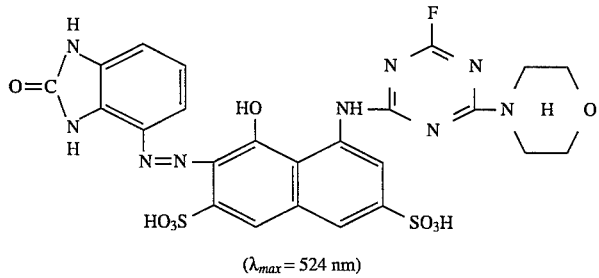

($\lambda_{max}$ = 524 nm)

and displays good fiber-reactive dye properties. For example, it dyes cotton in brilliant bluish red shades with good fastness properties by the dyeing and printing processes which are customary in the art.

EXAMPLE 5

59 parts of 2-(8'-hydroxy-3',6'-disulfo-1'-naphthylamino)-4-chloro-6-(3"-sulfophenylamino)-1,3,5-triazine and 29 parts of 4-(β-sulfatoethylsulfonyl)aniline are reacted with one another in 1000 parts of water at a pH of between 3 and 4 and at a temperature of between 85° and 95° C. over the course of four hours. The reaction solution is subsequently cooled to from 20° to 25° C. and, at a pH of between 6 and 7, the diazonium salt solution prepared from 14.9 parts of 5-aminobenzoimidazolidin-2-one in accordance with the indications of Example 1 is added. The mixture is subsequently stirred for a while in order to complete the coupling reaction.

The azo dye according to the invention which, written in the form of the free acid, has the formula

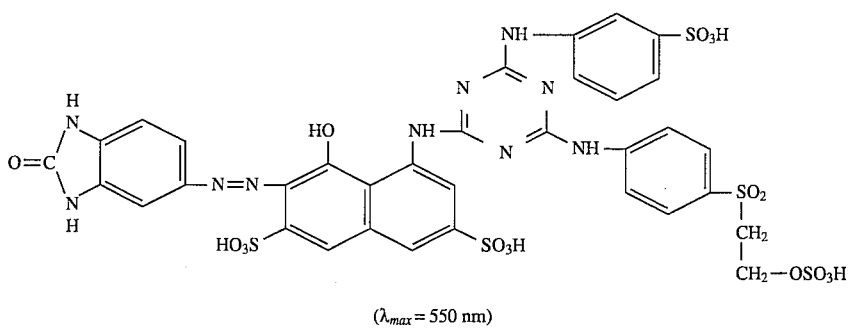

($\lambda_{max}$ = 550 nm)

is isolated in a customary manner as an alkali metal salt. It displays very good fiber-reactive properties and, for example, dyes cotton in brilliant violet shades with good fastness properties.

EXAMPLE 6

31.7 parts of 3-amino-4,6-disulfo-8-hydroxynaphthalene in 500 parts of water at a pH of between 2 and 2.5 and at a temperature of between 0° and 5° C. are reacted over the course of from 2 to 3 hours with 19 parts of cyanuric chloride. 36 parts of bis(β-chloroethylsulfonylethyl)amine hydrochloride are then added to the reaction mixture and the reaction is brought to completion with stirring at a pH of between 6 and 6.5 and at a temperature of between 40° and 50° C. Subsequently the mixture is cooled to from 20° to 25° C. and then, while maintaining a pH of between 6 and 7, a diazonium salt solution prepared from 14 parts of 5-aminobenzimidazoline-2-one in accordance with Example 1 is added. The mixture is subsequently stirred further for about 12 hours, after which the azo dye according to the invention which, written in the form of the free acid, has the formula

EXAMPLE 7

30 parts of 31% strength aqueous hydrochloric acid and 7 parts of sodium nitrite are added to 23 parts of 7-methoxy-6-aminoquinoxaline-2,3-dione in 300 parts of water at from 0° to 5° C. Stirring is continued until the diazotization is at an end and then the suspension of the diazonium salt is added to 1050 parts of an aqueous solution of 54.5 parts of the coupling component indicated in Example 2. The coupling reaction is carried out at a temperature of between 18° and 25° C. and at a pH of between 5 and 6 and the resulting azo compound which, written in the form of the free acid, has the formula

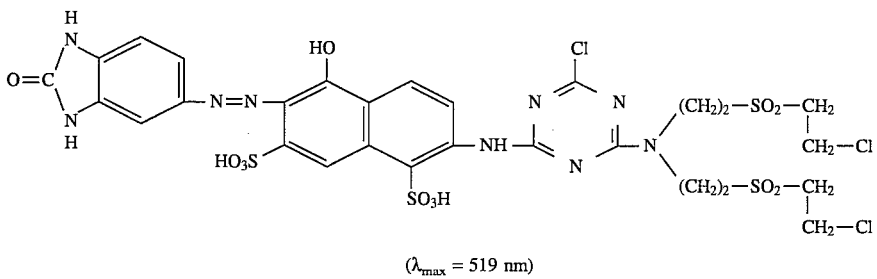

($\lambda_{max}$ = 519 nm)

is isolated in a customary manner as an alkali metal salt. It displays very good fiber-reactive dye properties and, for example, dyes cotton in red shades with good fastness properties.

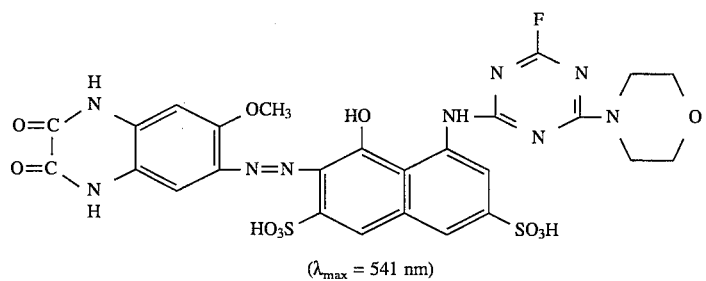

($\lambda_{max}$ = 541 nm)

is isolated in a customary manner from the synthesis solution, by salting out with sodium chloride. It possesses very good dye properties and, for example on cellulosic fiber materials, gives strong reddish-blue dyeings with a high degree of fixation.

EXAMPLE 8

A diazonium salt suspension prepared according to Example 7 from 23 parts of 7-methoxy-6-aminoquinoxaline-2,3-dione is stirred into a solution of 51.1 parts of the sodium salt of the compound 1-N-(2',4'-dichloro-1',3',5'-triazin-6'-yl)amino-8-hydroxy-3,6-disulfonaphthalene in 1000 parts of water and the coupling reaction is carried out at a temperature of between 18° and 25° C. and at a pH of from 5 to 6. The azo compound according to the invention is isolated from the synthesis solution in a customary manner, for example by salting out with sodium chloride. Written in the form of the free acid, it has the formula ing to the invention. Without isolating it from the aqueous synthesis solution, this solution is admixed after filtration with 30 parts of 31% strength aqueous hydrochloric acid, and the amino compound is diazotized in a customary manner using 7 parts of sodium nitrite. This diazonium salt suspension is then added, while maintaining a pH of from 5 to 6, to a solution of 77.8 parts of the sodium salt of the compound 1-N-[2'-(4"-β-sulfatoethylsulfonyl)-4'-chloro-1', 3',5'-triazin-6 -yl]amino-8-hydroxy-3,6-disulfonaphthalene in 500 parts of water. The coupling reaction is brought to completion at a pH of from 5 to 6 and at a temperature of between 18° and 25° C. and the azo compound according to the invention which is obtained, of the formula (written in the form of the free acid)

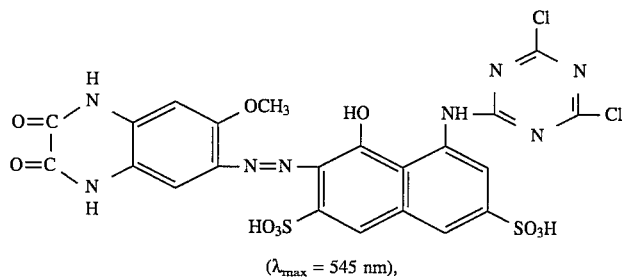

($\lambda_{max}$ = 545 nm), displays very good fiber-reactive dye properties and dyes cellulosic fiber materials, for example, in strong reddish blue shades with a high degree of fixation by the dyeing processes which are customary in the art.

EXAMPLE 9

9 parts of dimethyl carbonate are added at from 20° to 25° C. to 35.7 parts of the sodium salt of 4-(4'-sulfophenyl)amino- 3-aminonitrobenzene in 200 parts of water and the

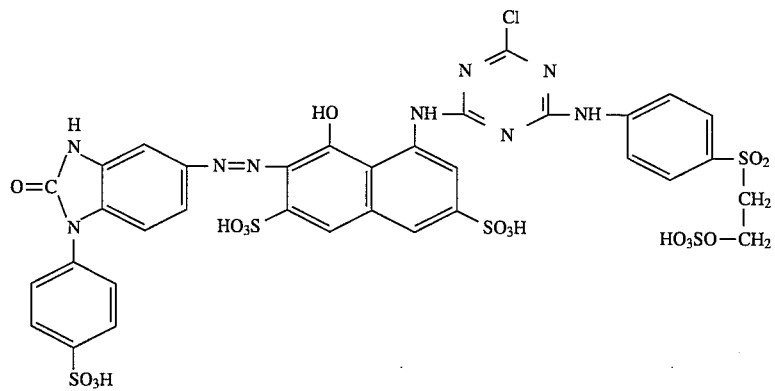

($\lambda_{max}$ = 550 nm)

mixture is stirred for a while at a pH of between 9 and 10 and at a temperature of from 80° to 90° C. The heterocyclic compound obtained is hydrogenated at a hydrogen pressure of 2 bar with the addition of customarily activated Raney nickel at a temperature of 60° C. and at a pH of 9.5.

The amino compound obtained is then used as a diazo component for the preparation of an azo compound accordis isolated, for example by salting out with sodium chloride.

The azo compound according to the invention, as a dye, gives strong dyeings and prints in violet shades with a high degree of fixation and with good fiber-reactive dye properties on cellulosic fiber materials, for example.

EXAMPLE 10

9 parts of dimethyl carbonate are added at from 20 to 25° C. to 51.9 parts of the sodium salt of the compound 4-(6',8'-disulfo-2'-naphthyl)amino-3-aminonitrobenzene in 200 parts of water. The reaction (cyclization) and subsequent hydrogenation of the nitro group to the amino group are carried out by analogy with the indications of Example 9. The resulting solution is filtered and 30 parts of 31% strength aqueous hydrochloric acid are added to the filtrate at from 0° to 5° C.; the compound is then diazotized in a customary manner using 7 parts of sodium nitrite. The resulting diazonium salt suspension is then added, while maintaining a pH of from 5 to 6, to a solution of 23.0 parts of 3-amino-8-hydroxy-6-sulfonaphthalene and the coupling reaction is brought to completion at from 18° to 25° C. and at a pH of from 5 to 6.

The azo compound obtained in this way is isolated by salting out with sodium chloride and is then dissolved in 500 parts of water. A suspension of 18 parts of cyanuric chloride in 150 parts of ice-water is added to this solution with thorough stirring at a temperature of from 0° to 5° C., and the mixture is maintained at a pH of from 5 to 6. After the end of the reaction, 27 parts of 4-(β-sulfatoethylsulfonyl)aniline are added, a pH of 6 is established and the reaction is brought to completion at 50° C. while maintaining this pH.

The azo compound according to the invention which is obtained, which has the formula (written in the form of the free acid)

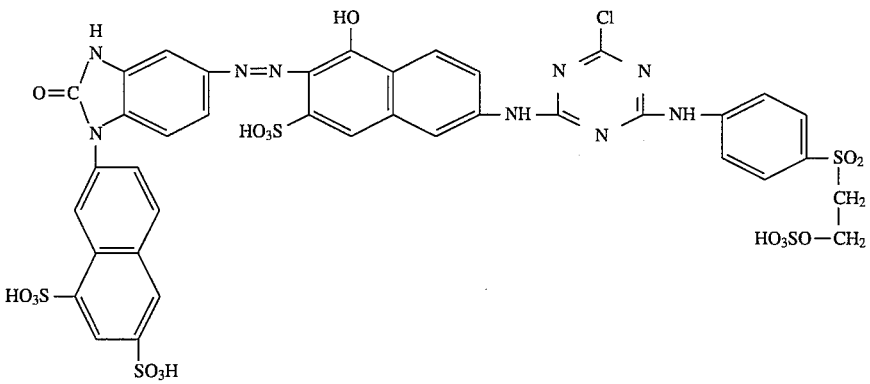

($\lambda_{max}$ = 532 nm)

is isolated in a customary manner, for example by spray-drying of the synthesis solution. It possesses very good fiber-reactive dye properties and dyes cellulosic fiber materials, for example, in strong red shades with a high degree of fixation.

EXAMPLE 11

12.6 parts of oxalyl dichloride are added to 35.7 parts of the sodium salt of the compound 4-(3'-sulfophenyl)amino-3-aminonitrobenzene in 200 parts of water at a temperature of from 10° to 15° C. The mixture is subsequently stirred further for a while at a pH of between 6 and 7 and at a temperature of initially from 30° to 40° C., then from 80° to 90° C., and, in the resulting heterocyclic compound, the nitro group is reduced to the amino group in a customary manner using activated Raney nickel at a hydrogen pressure of 2 bar, a temperature of from 40° to 60° C. and a pH of 9.

The resulting solution is freed from the Raney nickel by filtration and the dissolved amino compound is diazotized in a customary manner with 7 parts of sodium nitrite following the addition of 30 parts of 31% strength aqueous hydrochloric acid. The resulting diazonium salt suspension is added, while maintaining a pH of from 5 to 6, to a solution of 67.5 parts of the sodium salt of the compound 3-N-[2'-(4''-β-sulfatoethylsulfonyl)phenylamino- 4'-chloro-1',3',5'-triazin-6'-yl]amino-8-hydroxy-6-sulfonaphthalene in 500 parts of water. The coupling reaction is brought to completion at a pH of from 5 to 6 and at a temperature of from 18° to 25° C., after which the azo compound according to the invention is isolated in a customary manner, for example by salting out with sodium chloride.

Written in the form of the free acid, it has the formula

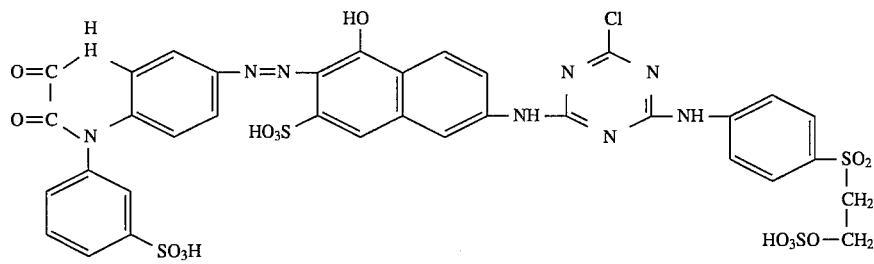

($\lambda_{max}$ = 540 nm).

It displays very good dye properties and dyes cellulosic fiber materials, for example, in strong red shades with a high degree of fixation by the dyeing and printing processes which are customary in the art for fiber-reactive dyes.

EXAMPLE 12

17.7 parts of 7-aminoquinazoline-2,4-dione (known from Egypt. J. Chem. 20, 427 (1980)) in 300 parts of water are diazotized, following the addition of 30 parts of 31% strength aqueous hydrochloric acid, in a customary manner using 7 parts of sodium nitrite at a temperature of from 0° to 5° C. The resulting diazonium salt suspension is then added to 1050 parts of an aqueous solution of 54.5 parts of the coupling component mentioned in Example 2, and the coupling reaction is carried out at from 18° to 25° C. and at a pH of from 5 to 6.

The azo compound according to the invention is isolated from the synthesis solution in a customary manner, for example by salting out with sodium chloride. Written in the form of the free acid it has the formula is carried out at from 18° to 25° C. and at a pH of between 5 and 6. The azo compound according to the invention is isolated from the aqueous synthesis solution, for example, by salting out. Written in the form of the free acid it has the formula

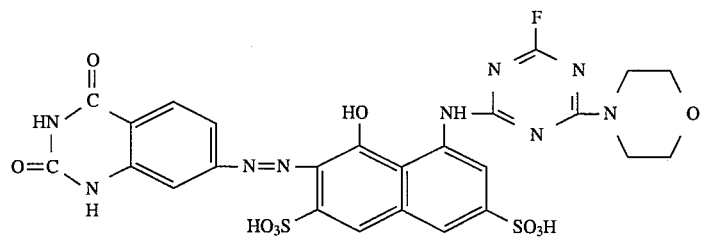

($\lambda_{max}$ = 525 nm)

and gives strong, brilliant red dyeings with a high degree of fixation, for example on cellulosic fiber materials such as

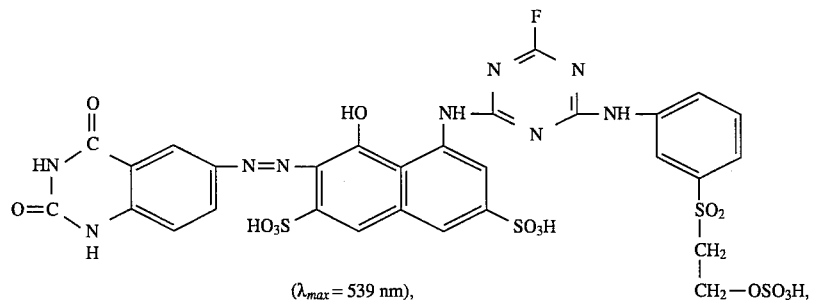

($\lambda_{max}$ = 539 nm), cotton, by the dyeing processes which are customary for fiber-reactive dyes.

EXAMPLE 13

17.7 parts of 6-aminoquinazoline-2,4-dione (known from Egypt. J. Chem., loc. cit.) are diazotized by analogy with the indications of Example 12 and the resulting diazonium salt suspension is added to a solution of 77.8 parts of the compound 1-N-[2'-(3"-β-sulfatoethylsulfonyl)phenylamino-4'-chloro-1',3',5'-triazin-6'-yl]amino 8-hydroxy-3,6-disulfonaphthalene in 1000 parts of water. The coupling reaction displays very good fiber-reactive dye properties and dyes cellulosic fiber materials such as cotton, for example, in strong, brilliant bluish red shades with a high degree of fixation by the application methods which are customary in the art for fiber-reactive dyes.

EXAMPLE 14

16.7 parts of 7-amino-3,4-dihydroquinolin-2-one (known from J. Chem. Soc. C 1969, 183) are diazotized by analogy with the indications of Example 12. The resulting diazonium salt suspension is then stirred at a pH of from 5 to 6 into a solution of 23 parts of 3-amino-8-hydroxy-6-sulfonaphthalene in 500 parts of water and the coupling reaction is carried out in this pH range and at from 18° to 25° C. The resulting aminoazo compound is isolated by salting out with sodium chloride and is dissolved in 500 parts of water. 15 parts of cyanuric fluoride are added with intense stirring at from 0° to 3° C., while maintaining a pH of above 4, and the reaction is then brought to completion at from 0° to 3° C. and at a pH of 5. The second condensation reaction with the difluorotriazinylamino compound obtained is then carried out, following adjustment of the pH to 6, by addition of 27 parts of 3-(β-chloroethylsulfonyl)propylamine at a pH of from 8 to 9 and at a temperature of from 10° to 15° C.

The azo compound according to the invention of the formula (written in the form of the free acid)

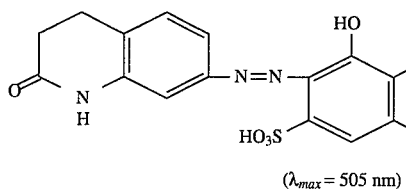

($\lambda_{max}$ = 505 nm)

is isolated from the aqueous synthesis solution in a customary manner, for example by salting out with sodium chloride. It displays very good dye properties and gives strong dyeings and prints in brilliant red shades with a high degree of fixation on, for example, the materials mentioned in the description, especially cellulosic fiber materials such as, for example, cotton, by the dyeing and printing processes which are customary in the art for fiber-reactive dyes.

EXAMPLE 15

14.8 parts of 6-amino-1,3-dihydroindol-2-one (known from EP-A-0,549,892) are diazotized by analogy with the indications of Example 12. The diazonium salt suspension is then added to 1050 parts of an aqueous solution of 54.5 parts of the compound 2-N-{2'-[N'-phenyl-N'-γ-(β'-sulfatoethylsulfonyl)propyl]amino-4'-fluoro-1',3',5'-triazin-6'-yl}amino-8-hydroxy-6-sulfonaphthalene and the coupling reaction is brought to completion with thorough stirring at from 18° to 25° C. and at a pH of from 5 to 6.

The azo compound according to the invention of the formula (written in the form of the free acid)

EXAMPLE 16

19.8 parts of 5-amino-1,2-benzoisothiazoline-3-one 1,1-dioxide (known from J. Macromol. Sci. 3, 941 (1969)) are diazotized by analogy with the indications of Example 12 and the resulting diazonium salt suspension is stirred into 500 parts of an aqueous solution of 24 parts of 3-amino-8-hydroxy-6-sulfonaphthalene, establishing a pH of between 5 and 6 using sodium carbonate and bringing the coupling reaction to completion within this pH range and at a temperature of between 18° and 25° C.

The aminoazo compound which is obtained is isolated from the aqueous synthesis solution by salting out with sodium chloride and is then dissolved in 1000 parts of water, with thorough stirring and addition of a commercially available dispersant. 42 parts of the compound N-phenyl-N-(2,4-difluoro-1,3,5-triazin-6-yl)-N-[β-(β'-sulfatoethylsulfonyl)ethyl]amine (known from EP-A-0,568,876) are added; the reaction is carried out at a temperature of from 10° to 15° C. and at a pH of 6.

The azo compound according to the invention of the formula (written in the form of the free acid)

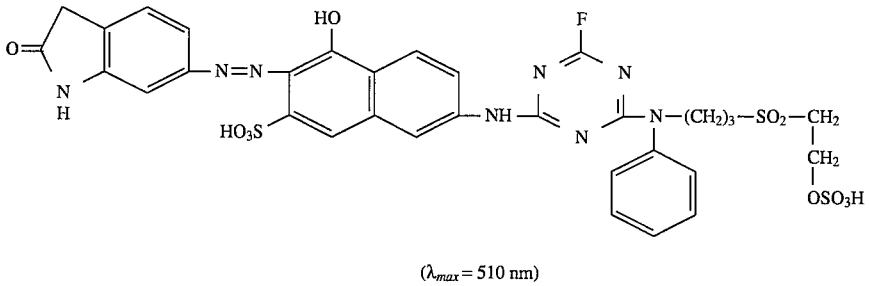

($\lambda_{max}$ = 510 nm)

is isolated in a customary manner by salting out with sodium chloride. It displays good dye properties and dyes cellulosic fiber materials such as cotton, for example, in strong, brilliant red shades with a high degree of fixation.

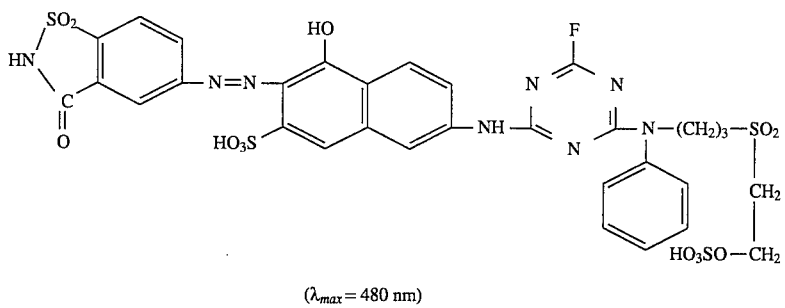

($\lambda_{max}$ = 480 nm)

EXAMPLE 17

19.8 parts of 6-amino-1,2-benzoisothiazolin-3-one 1,1-dioxide (known from J. Chem. Educ. 47, 649 (1970)) are diazotized by analogy with the indications of Example 12 and the resulting diazonium salt suspension is stirred into 1050 parts of an aqueous solution of 57.5 parts of the sodium salt of the compound 3-N-{2'-[N'-phenyl-N'-β-(β'-sulfatoethylsulfonyl)ethyl]amino-4'-fluoro-1',3',5'-triazin-6'-yl}amino-8-hydroxy-6-sulfonaphthalene and the reaction is brought to completion with further stirring at a pH of between 5 and 6 and at a temperature of from 18° to 20° C.

The azo compound according to the invention which is obtained, of the formula (written in the form of the free acid)

description, in particular cellulosic fiber materials such as, for example, cotton.

EXAMPLE 18

30 parts of 31% strength aqueous hydrochloric acid are added to 18.5 parts of 5-chloro-6-aminobenzoxazolin-2-one (known from DE-C-43 96 06) in 300 parts of water and the mixture is diazotized in a customary manner using 7 parts of sodium nitrite. The resulting diazonium salt suspension is then stirred into 1050 parts of an aqueous solution of 65 parts of the compound 3-N-{2'-[3"-(β-sulfatoethyl)sulfonyl)phenyl]amino-4'-cyanoamino-1',3',5'-triazin-6'-yl}amino-8-hydroxy-6-sulfonaphthalene and the coupling reaction is carried out with stirring from 18° to 25° C. and at a pH of from 5 to 6.

The azo compound according to the invention of the formula (written in the form of the free acid)

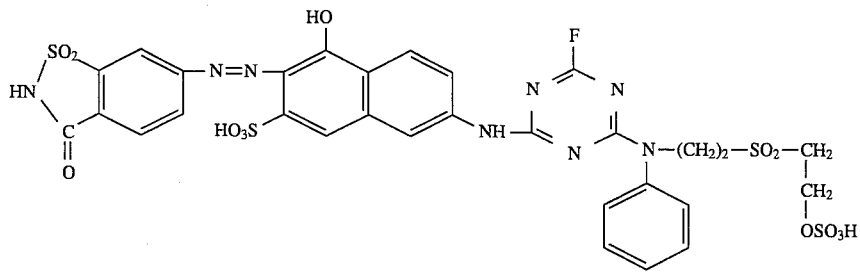

($\lambda_{max}$ = 486 nm)

can be isolated in a customary manner, for example by salting out with sodium chloride. It displays good dye properties and gives strong, brilliant orange dyeings with a high degree of fixation on the materials mentioned in the

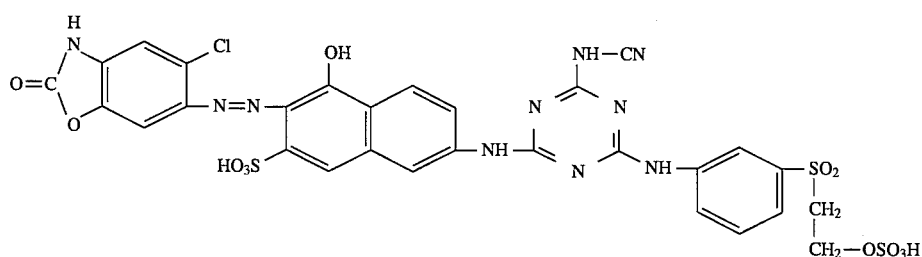

($\lambda_{max}$ = 539 nm)

is isolated using sodium chloride. It can be used by the dyeing and printing processes which are customary in the art for fiber-reactive dyes to obtain, on the fiber materials mentioned in the description such as, for example, cellulosic fiber materials such as cotton, strong, brilliant red dyeings and prints with a high degree of fixation.

EXAMPLE 19

16.2 parts of 5-aminophthalimide in 530 parts of an aqueous solution containing hydrochloric acid are diazotized by analogy with the indications of Example 12 using 7 parts of sodium nitrite and the resulting diazonium salt suspension is stirred, while maintaining a pH of from 5 to 6, into 1050 parts of an aqueous solution of 75.5 parts of the compound 3-N-{2'-[3"-(β-sulfatoethylsulfonyl)phenyl] amino-4'-chloro-1',3',5'-triazin-6'-yl}amino-8-hydroxy-4,6-disulfonaphthalene and the coupling reaction is brought to completion within this pH range and at from 18° to 25° C. The azo dye according to the invention is isolated from the synthesis solution by salting out with sodium chloride. Written in the form of the free acid it has the formula

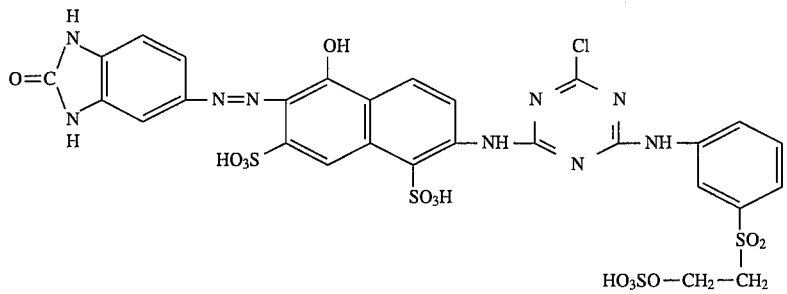

($\lambda_{max}$ = 495 nm).

It gives strong, brilliant yellowish red dyeings and prints with a high degree of fixation on cellulosic fiber materials, for example, by the dyeing and printing processes which are customary in the art for fiber-reactive dyes.

EXAMPLES 20 TO 36

In the Tabular Examples below, further azo compounds according to the invention of the formula (A)

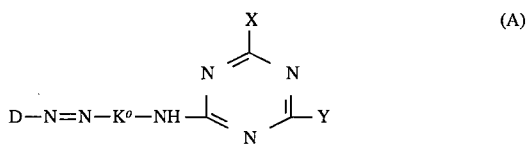

are described by means of their formula components, They can be prepared in the manner according to the invention, for example according to one of the above Examples, by means of the components which are evident from each Tabular Example in conjunction with the formula (A) (the diazo component D-NH$_2$, the coupling component H—K$^o$—NH$_2$, cyanuric fluoride or cyanuric chloride, if desired an amino compound H-X and a compound H-Y). They possess very good fiber-reactive dye properties and give strong, fast dyeings and prints in the shade indicated for dyeings on cotton in the respective tabular example when applied to the materials mentioned in the description, especially cellulosic fiber materials such as cotton, by the known dyeing and printing processes.

| | | Azo compound of the formula (A) | | | |
|---|---|---|---|---|---|
| Ex. | Radical D— | Radical —K°— | Radical X | Radical Y | Shade |
| 20 | Benzimidazolin-2-on-5-yl | 3,6-Disulfo-8-hydroxy-naphth-7,1-ylene | Chlorine | 4-(β-Sulfato-ethylsulfonyl)phenylamino | violet (547) |
| 21 | Benzimidazolin-2-on-5-yl | 3,6-Disulfo-8-hydroxy-naphth-7,1-ylene | Fluorine | 3-Sulfophenylamino | violet (551) |
| 22 | Benzimidazolin-2-on-5-yl | 6-Sulfo-8-hydrox-naphth-7,3-ylene | Chlorine | " | red (520) |
| 23 | Benzimidazolin-2-on-5-yl | 6-Sulfo-8-hydrox-naphth-7,3-ylene | Chlorine | 4,6,8-Trisulfonaphth-2-yl-amino | red (520) |
| 24 | Benzimidazolin-2-on-5-yl | 6-Sulfo-8-hydrox-naphth-7,3-ylene | 3-Sulfophenyl-amino | 4-(β-Sulfatoethylsul-fonyl)phenylaino | red (520) |
| 25 | Benzimidazolin-2-on-5-yl | 6-Sulfo-8-hydrox-naphth-7,3-ylene | Chlorine | 2-Sulfo-4-(β-sulfatoethyl-sulfonyl)phenylamino | red (520) |
| 26 | Benzimidazolin-2-on-5-yl | 4,6-Disulfo-8-hydroxy-naphth-7,3-ylene | Chlorine | 2-Sulfo-4-(β-sulfatoethyl-sulfonyl)phenylamino | red (522) |

-continued

Azo compound of the formula (A)

| Ex. | Radical D— | Radical —K°— | Radical X | Radical Y | Shade |
|---|---|---|---|---|---|
| 27 | Benzimidazolin-2-on-5-yl | 6-Sulfo-8-hydroxy-naphth-7,2-ylene | Chlorine | 2,5-Disulfophanylamino | red (527) |
| 28 | Benzimidazolin-2-on-5-yl | 3,6-Disulfo-8-hydroxy-naphth-7,1-ylene | Chlorine | " | bluish-red (545) |
| 29 | Benzimidazolin-2-on-5-yl | 4,6-Disulfo-8-hydroxy-naphth-7,3-ylene | Chlorine | N-Phenyl-N-[(β'-sulfato-ethylsulfonyl)propyl]amino | red (521) |
| 30 | Benzimidazolin-2-on-5-yl | 4,6-Disulfo-8-hydroxy-naphth-7,3-ylene | Chlorine | γ-(β'-Sulfatoethylsul-fonyl)propylamino | red (520) |
| 31 | Benzimidazolin-2-on-5-yl | 4,6-Disulfo-8-hydroxy-naphth-7,3-ylene | Chlorine | bis-[γ-(β'-Sulfatoethyl-sulfonyl)propyl]amino | red (519) |
| 32 | Benzimidazolin-2-on-4-yl | 4,6-Disulfo-8-hydroxy-naphth-7,3-ylene | Chlorine | Morpholino | bluish red (525/550) |
| 33 | Benzimidazolin-2-on-4-yl | 6-Sulfo-8-hydroxy-naphth-7,3-ylene | Chlorine | 3-Sulfophenylamino | yellowish red (502) |
| 34 | Benzimidazolin-2-on-5-yl | 4,6-Disulfo-8-hydroxy-7,1-ylene | Fluorine | Morpholino | bluish red (526/550) |
| 35 | 7-Methylquinoxaline-2,3-dion-6-yl | 3,6-Disulfo-8-hydroxy-7,1-ylene | Fluorine | Morpholino | violet (535) |
| 36 | 7-Ethoxyquinoxaline-2,3-dion-6-yl | 3,6-Disulfo-8-hydroxy-7,1-ylene | Fluorine | Morpholino | reddish blue (542) |

We claim:

1. An azo compound of the formula (1)

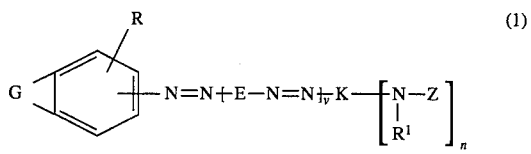

in which

G forms to the benzene ring the radical of a heterocycle which is free from olefinic double bonds and which contains at least one carboxamide group of the formula —CO—N($R^{10}$)— in which $R^{10}$ is hydrogen, alkyl of 1 to 4 carbon atoms, or aryl of 6 to 10 carbon atoms optionally substituted by 1, 2 or 3 substituents from the group consisting of sulfo, carboxy, alkoxy of 1 to 4 carbon atoms, alkyl of 1 to 4 carbon atoms, halogen, cyano, nitro and amino, and which optionally contains 1 or 2 further hetero-groups selected from —O—, —S— and —N($R^{10}$)— where $R^{10}$ is as defined above;

R is hydrogen, alkyl of 1 to 4 carbon atoms, alkoxy of 1 to 4 carbon atoms, halogen or sulfo;

$R^1$ is hydrogen, alkyl of 1 to 4 carbon atoms or alkyl of 1 to 4 carbon atoms which is substituted by hydroxy, cyano, alkoxy of 1 to 4 carbon atoms, carboxy, sulfo, sulfato or phosphato, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms;

E is the bivalent radical, free from the amino group, of a compound from the aniline or naphthyl amine series which is capable of coupling and can be diazotized;

v is the number zero, 1 or 2,

K is the bivalent radical, free from the amino group, of a coupling component from the aniline or naphthylamine series or the bivalent radical of a coupling component from the heterocyclic series;

n is the number 1, 2, 3 or 4;

Z is a radical of the formula (3)

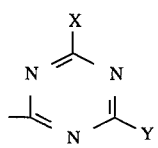

in which

X is halogen or a group of the formula (4)

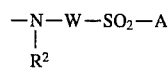

in which $R^2$ is hydrogen, alkyl of 1 to 4 carbon atoms or alkyl of 1 to 4 carbon atoms substituted by hydroxy, cyano, alkoxy of 1 to 4 carbon atoms, carboxy, sulfo, sulfato or phosphato, or is phenyl, naphthyl, or phenyl or naphthyl, each being substituted by 1, 2 or 3 substituents selected from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms, W is alkylene of 2 to 4 carbon atoms, or alkylene of 3 to 6 carbon atoms interrupted by 1 or 2 hetero-groups selected from the group consisting of the formulae —O—, —NH—, —$SO_2$—, —CO— and —N($R^{10}$)— where $R^{10}$ is as defined above, or W is phenylene, naphthylene, or phenylene or naphthylene each substituted by 1, 2 or 3 substituents selected from the group consisting of halogen, hydroxy, cyano, nitro, alkoxy of 1 to 4 carbon atoms, alkyl of 1 to 4 carbon atoms, alkoxycarbonyl of 2 to 5 carbon atoms, carboxy, sulfamoyl and sulfo, and A is vinyl or is ethyl which is substituted in the β-position by a substituent which is eliminated under the action of alkali to form the vinyl group;

Y is chlorine, cyanoamino or a group of the formula (5)

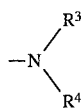     (5)

in which

R³ is hydrogen, alkyl of 1 to 4 carbon atoms or alkyl of 4 to 4 carbon atoms substituted by halogen, hydroxy, cyano, alkoxy of 1 to 4 carbon atoms, alkoxycarbonyl of 2 to 5 carbon atoms, carboxy, sulfo, sulfato or phosphato, or is a group of the formula —W—SO₂-A where W and A are as defined above, and R⁴ is hydrogen, alkyl of 1 to 4 carbon atoms or alkyl of 1 to 4 carbon atoms substituted by halogen, hydroxy, cyano, alkoxy of 1 to 4 carbon atoms, alkoxycarbonyl of 2 to 5 carbon atoms, carboxy, sulfo, sulfato or phosphato, or is cycloalkyl of 5 to 8 carbon atoms or a group of the formula —W—SO₂-A where W and A are as defined above, or is phenyl, naphthyl, or phenyl or naphthhyl each substituted by 1, 2 or 3 substituents selected from the group consisting of halogen, hydroxy, cyano, alkoxy of 1 to 4 carbon atoms, alkyl of 1 to 4 carbon atoms, alkoxycarbonyl of 2 to 4 carbon atoms, carboxy, sulfamoyl, sulfo and alkylsulfonyl having an alkyl radical of 1 to 4 carbon atoms, or R³ and R⁴ together are an alkylene of 3 to 6 carbon atoms or an alkylene of 3 to 6 carbon atoms which is interrupted by a group —NH—, —O—, —CO—, —S—, —SO₂— or —N(R⁵)— (in which R⁵ is sulfo- or sulfato-substituted alkyl of 1 to 4 carbon atoms) and which together with the nitrogen atom form a heterocyclic radical, or Z is difluorochloropyrimidino, trichloropyrimidino, methylsulfonylchloropyrimidino, methylfluorochloropyrimidino or dichloroquinoxalino; and the compound of the formula (1) possesses at least one sulfo group.

2. An azo compound as claimed in claim 1, wherein G is a radical of the formula (2a), (2b), (2c), (2d), (2e), (2f), (2g) or (2h)

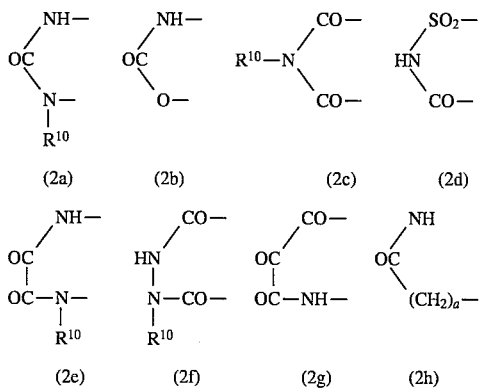

in which R¹⁰ is as defined in claim 1 and in formula (2h) the index a is the number 1 or 2.

3. An azo compound as claimed in claim 1, wherein Z is a radical of the formula (3)

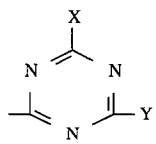     (3)

in which:

X is halogen or a group of the formula (4)

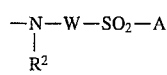     (4)

in which

R² is hydrogen or alkyl of 1 to 4 carbon atoms or alkyl of 1 to 4 carbon atoms which is substituted by hydroxy, cyano, alkoxy of 1 to 4 carbon atoms, carboxy, sulfo, sulfato or phosphato, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms, W is alkylene of 2 to 4 carbon atoms or is alkylene of 3 to 6 carbon atoms which is interrupted by 1 or 2 hetero-groups selected from the groups of the formulae —O—, —NH—, —SO₂—, —CO— and —N(R¹⁰)— where R¹⁰ is as defined in claim 1, or is phenylene or naphthylene, each of which may be substituted by 1, 2 or 3 substituents from the group consisting of halogen, hydroxy, cyano, nitro, alkoxy of 1 to 4 carbon atoms, alkyl of 1 to 4 carbon atoms, alkoxycarbonyl of 2 to 5 carbon atoms, carboxy, sulfamoyl and sulfo, or is phenylenealkylene or alkylenephenylene having an alkylene of in each case 1 to 4 carbon atoms, and A is vinyl or is ethyl which is substituted in the β position by a substituent which can be eliminated under the action of alkali to form the vinyl group;

Y is chlorine, cyanoamino or a group of the formula (5)

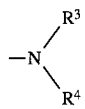     (5)

in which

R³ is hydrogen or alkyl of 1 to 4 carbon atoms or alkyl of 1 to 4 carbon atoms which is substituted by halogen, hydroxy, cyano, alkoxy of 1 to 4 carbon atoms, alkoxycarbonyl of 2 to 5 carbon atoms, carboxy, sulfo, sulfato or phosphato, or is a group of the formula —W—SO₂-A where W and A are as defined above, and R⁴ is hydrogen or alkyl of 1 to 4 carbon atoms or alkyl of 1 to 4 carbon atoms which is substituted by halogen, hydroxy, cyano, alkoxy of 1 to 4 carbon atoms, alkoxycarbonyl of 2 to 5 carbon atoms, carboxy, sulfo, sulfato or phosphato, or is cycloalkyl of 5 to 8 carbon atoms or is a group of the formula —W—SO₂-A where W and A are as defined above, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms, or $R^3$ and $R^4$ together are an alkylene of 3 to 6 carbon atoms or an alkylene of 3 to 6 carbon atoms which is interrupted by a group —NH—, —O—, —CO—, —S—, —SO$_2$— or —N(R$^5$)— (in which $R^5$ is sulfo- or sulfato-substituted alkyl of 1 to 4 carbon atoms) which together with the nitrogen atom form a heterocyclic radical.

4. An azo compound as claimed in claim 1, wherein $R^1$ is hydrogen, methyl or ethyl.

5. An azo compound as claimed in claim 1, wherein X is chlorine or fluorine.

6. An azo compound as claimed in claim 1, wherein Y is a group of the formula (4)

$$-\underset{\underset{R^2}{|}}{N}-W-SO_2-A \quad (4)$$

in which $R^2$ is hydrogen, alkyl of 1 to 4 carbon atoms or alkyl of 1 to 4 carbon atoms which is substituted by hydroxy, cyano, alkoxy of 1 to 4 carbon atoms, carboxy, sulfo, sulfato or phosphato, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms, W is alkylene of 2 to 4 carbon atoms or is alkylene of 3 to 6 carbon atoms which is interrupted by 1 or 2 hetero-groups selected from the groups of the formulae —O—, —NH—, —SO$_2$—, —CO— and —N(R$^{10}$)— where $R^{10}$ is as defined in claim 1, or is phenylene or naphthylene, each of which may be substituted by 1, 2 or 3 substituents from the group consisting of halogen, hydroxy, cyano, nitro, alkoxy of 1 to 4 carbon atoms, alkyl of 1 to 4 carbon atoms, alkoxycarbonyl of 2 to 5 carbon atoms, carboxy, sulfamoyl and sulfo, or is phenylenealkylene or alkylenephenylene having an alkylene of in each case 1 to 4 carbon atoms, and A is vinyl or is ethyl which is substituted in the β position by a substituent which can be eliminated under the action of alkali to form the vinyl group.

7. An azo compound as claimed in claim 1, wherein Y is morpholino.

8. An azo compound as claimed in claim 1, wherein Y is mono- or disulfophenyl or mono-, di- or trisulfonaphthyl.

9. An azo compound of the formula (1)

$$G\begin{array}{c}R\\ \diagup\end{array}-N=N+E-N=N+_v K-\left[\underset{\underset{R^1}{|}}{N}-Z\right]_n \quad (1)$$

in which

G forms to the benzene ring the radical of a heterocycle which is free from olefinic double bonds and which contains at least one carboxamide group of the formula —CO—N(R$^{10}$)— in which $R^{10}$ is hydrogen, alkyl of 1 to 4 carbon atoms, or aryl of 6 to 10 carbon atoms optionally substituted by 1, 2 or 3 substituents from the group consisting of sulfo, carboxy, alkoxy of 1 to 4 carbon atoms, alkyl of 1 to 4 carbon atoms, halogen, cyano, nitro and amino, and which optionally contains 1 or 2 further hetero-groups selected from —O—, —S— and —N(R$^{10}$)— where $R^{10}$ is as defined above;

R is hydrogen, alkyl of 1 to 4 carbon atoms, alkoxy of 1 to 4 carbon atoms, halogen or sulfo;

$R^1$ is hydrogen, alkyl of 1 to 4 carbon atoms or alkyl of 1 to 4 carbon atoms which is substituted by hydroxy, cyano, alkoxy of 1 to 4 carbon atoms, carboxy, sulfo, sulfato or phosphato, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms;

E is the bivalent radical, free from the amino group, of a compound from the aniline or naphthylamine series which is capable of coupling and can be diazotized;

v is the number zero, 1 or 2,

Z is the bivalent radical, free from the amino group, of a coupling component from the aniline or naphthylamine series or the bivalent radical or a coupling component from the heterocyclic series;

n is the number 1, 2, 3 or 4;

wherein

Z is a radical of the formula (8a)

$$\begin{array}{c}X\\ \diagup\diagdown\\ N\quad\quad N\\ \|\quad\quad\|\\ \diagdown\diagup-\underset{\underset{R^2}{|}}{N}-W^1-SO_2-A\\ N\end{array} \quad (8a)$$

in which X is chlorine, fluorine or cyanoamino, A is vinyl or is ethyl which is substituted in the β position by a substituent which can be eliminated under the action of alkali to form the vinyl group, $R^2$ is hydrogen, ethyl, methyl, β-hydroxyethyl, β-sulfatoethyl, phenyl, 3-sulfophenyl or 4-sulfophenyl and $W^1$ is 1,2-ethylene, 1,3-propylene, 2-methyl-1,2-ethylene, 2-methyl-1,3-propylene, 1,4-phenylene, 1,3-phenylene, 2-methoxy-1,5-phenylene, 2,5-dimethoxy-1,4-phenylene, 2-methoxy-5-methyl-1,4-phenylene, 2-sulfo-1,4-phenylene, 2-hydroxy-1,5-phenylene, 2-bromo-1,5-phenylene or 4-(2' -eth)phen-1,1'-ylene, in which groups position 1 is attached to the nitrogen atom, or is 1-sulfonaphth-2, 6-ylene or naphth-2,8-ylene, in which groups position is attached to the nitrogen atom; and wherein the compound of the formula (1) possesses at least one sulfo group.

10. An azo compound as claimed in claim 1, wherein the compound is of the formula (1A)

$$\begin{array}{c}H\\ |\\ N\\ \diagup\diagdown\\ O=C\\ \diagdown\diagup\\ B\end{array}-N=N+E-N=N+_v K-\left[\underset{\underset{R^1}{|}}{N}-Z\right]_n \quad (1A)$$

in which

E is the bivalent radical, free from the amino group, of a compound from the aniline or naphthylamine series which is capable of coupling and can be diazotized;

v is the number zero, 1 or 2;

K is the bivalent radical, free from the amino group, of a coupling component from the aniline or naphthylamine series or the bivalent radical of a coupling component from the heterocyclic series;

R¹ is hydrogen, alkyl of 1 to 4 carbon atoms or alkyl of 1 to 4 carbon atoms which is substituted by hydroxy, cyano, alkoxy of 1 to 4 carbon atoms, carboxy, sulfo, sulfato or phosphato, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms;

n is the number 1, 2, 3 or 4;

Z is as defined in claim 1; and B is —O— or —N(R¹⁰)—, in which R¹⁰ is hydrogen phenyl monosulfophenyl, disulfophenyl, trisulfophenyl, naphthyl, monosulfonaphthyl, disulfonaphthyl or trisulfonaphthyl.

11. An azo compound as claimed in claim 1, wherein the compound is of the formula (1B)

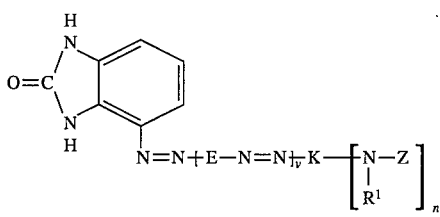

in which

E is the bivalent radical, free from the amino group, of a compound from the aniline or naphthylamine series which is capable of coupling and can be diazotized;

v is the number zero, 1 or 2;

K is the bivalent radical, free from the amino group, of a coupling component from the aniline or naphthylamine series or the bivalent radical of a coupling component from the heterocyclic series;

R¹ is hydrogen, alkyl of 1 to 4 carbon atoms or alkyl of 1 to 4 carbon atoms which is substituted by hydroxy, cyano, alkoxy of 1 to 4 carbon atoms, carboxy, sulfo, sulfato or phosphato, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms;

n is the number 1, 2, 3 or 4;

Z is as defined in claim 1.

12. An azo compound as claimed in claim 1, wherein the compound is of the formula (1C)

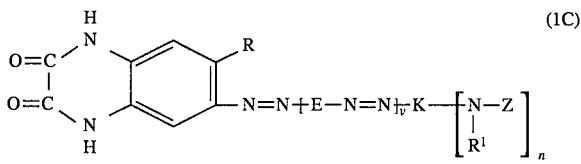

in which

E is the bivalent radical, free from the amino group, of a compound from the aniline or naphthylamine series which is capable of coupling and can be diazotized;

v is the number zero, 1 or 2;

K is the bivalent radical, free from the amino group, of a coupling component from the aniline or naphthylamine series or the bivalent radical of a coupling component from the heterocyclic series;

R¹ is hydrogen, alkyl of 1 to 4 carbon atoms or alkyl of 1 to 4 carbon atoms which is substituted by hydroxy, cyano, alkoxy of 1 to 4 carbon atoms, carboxy, sulfo, sulfato or phosphato, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms;

n is the number 1, 2, 3 or 4;

Z is as defined in claim 1;

and R is hydrogen, methyl or methoxy.

13. An azo compound as claimed in claim 1, wherein the compound is of the formula (1E)

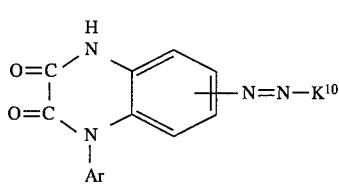

in which Ar is phenyl substituted by 1 or 2 sulfo groups or is naphthyl substituted by 1, 2 or 3 sulfo groups and $K^{10}$ is a group of the formula (8A)

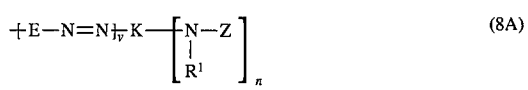

in which

E is the bivalent radical, free from the amino group, of a compound from the aniline or naphthylamine series which is capable of coupling and can be diazotized;

v is the number zero, 1 or 2;

K is the bivalent radical, free from the amino group, of a coupling component from the aniline or naphthylamine series or the bivalent radical of a coupling component from the heterocyclic series;

R¹ is hydrogen, alkyl of 1 to 4 carbon atoms or alkyl of 1 to 4 carbon atoms which is substituted by hydroxy, cyano, alkoxy of 1 to 4 carbon atoms, carboxy, sulfo, sulfato or phosphate, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms;

n is the number 1, 2, 3 or 4;

Z is as defined in claim 1.

14. An azo compound as claimed in claim 1, wherein the compound is of the formula (1F)

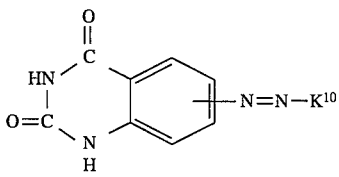

in which $K^{10}$ is a group of the formula (8A)

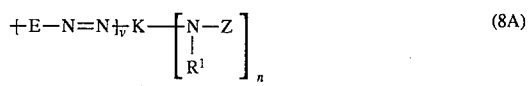

in which

E is the bivalent radical, free from the amino group, of a compound from the aniline or naphthylamine series which is capable of coupling and can be diazotized;

v is the number zero, 1 or 2;

K is the bivalent radical, free from the amino group, of a coupling component from the aniline or naphthylamine series or the bivalent radical of a coupling component from the heterocyclic series;

$R^1$ is hydrogen, alkyl of 1 o 4 carbon atoms or alkyl of 1 to 4 carbon atoms which is substituted by hydroxy, cyano, alkoxy of 1 to 4 carbon atoms, carboxy, sulfo, sulfato or phosphato, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms;

n is the number 1, 2, 3 or 4;

Z is as defined in claim 1.

15. An azo compound as claimed in claim 1, wherein the compound is of the formula (1G)

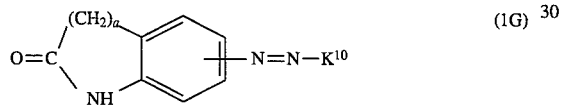

in which a is the number 1 or 2 and $K^{10}$ is a group of the formula (8A)

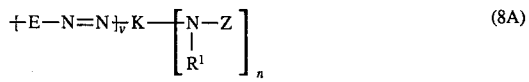

in which

E is the bivalent radical, free from the amino group, of a compound from the aniline or naphthylamine series which is capable of coupling and can be diazotized;

v is the number zero, 1 or 2;

K is the bivalent radical, free from the amino group, of a coupling component from the aniline or naphthylamine series or the bivalent radical of a coupling component from the heterocyclic series;

$R^1$ is hydrogen, alkyl of 1 to 4 carbon atoms or alkyl of 1 to 4 carbon atoms which is substituted by hydroxy, cyano, alkoxy of 1 to 4 carbon atoms, carboxy, sulfo, sulfato or phosphato, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms;

n is the number 1, 2, 3 or 4;

Z is as defined in claim 1.

16. An azo compound as claimed in claim 1, wherein the compound is of the formula (1H)

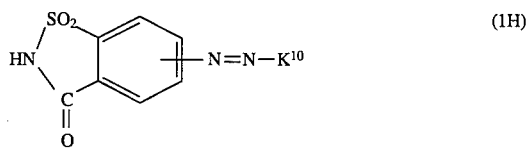

in which $K^{10}$ is a group of the formula (8A)

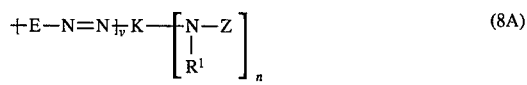

in which

E is the bivalent radical, free from the amino group, of a compound from the aniline or naphthylamine series which is capable of coupling and can be diazotized;

v is the number zero, 1 or 2;

K is the bivalent radical, free from the amino group, of a coupling component from the aniline or naphthylamine series or the bivalent radical of a coupling component from the heterocyclic series;

$R^1$ is hydrogen, alkyl of 1 to 4 carbon atoms or alkyl of 1 to 4 carbon atoms which is substituted by hydroxy, cyano, alkoxy of 1 to 4 carbon atoms, carboxy, sulfo, sulfato or phosphato, or is phenyl or naphthyl, each of which may be substituted by 1, 2 or 3 substituents from the group consisting of halogen, hydroxy, cyano, alkoxy of 1 to 4 carbon atoms, alkyl of 1 to 4 carbon atoms, alkoxycarbonyl of 2 to 5 carbon atoms, carboxy, sulfamoyl, sulfo and alkylsulfonyl having an alkyl radical of 1 to 4 carbon atoms;

n is the number 1, 2, 3 or 4;

Z is as defined in claim 1.

17. The azo compound of claim 3, wherein $R^5$ is sulfo- or sulfato-substituted alkyl of 2 carbon atoms.

18. A process for dyeing a material which contains hydroxy and/or carboxamido groups, which comprises the step of contacting the material with a dye as claimed in claim 1.

19. A process for the dyeing a material which contains hydroxy or carboxamido groups, in which a dye is applied to the material and the dye is fixed on the material by means of heat or by means of an alkaline agent or by means of both measures, wherein the dye employed is a dye of claim 1.

* * * * *